(12) United States Patent
Clinton

(10) Patent No.: US 11,058,303 B2
(45) Date of Patent: Jul. 13, 2021

(54) SYSTEM AND METHOD FOR DETERMINING STABILITY OF CARDIAC OUTPUT

(71) Applicant: COVIDIEN LP, Mansfield, MA (US)

(72) Inventor: Matt Clinton, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1262 days.

(21) Appl. No.: 14/886,922

(22) Filed: Oct. 19, 2015

(65) Prior Publication Data

US 2016/0038041 A1    Feb. 11, 2016

Related U.S. Application Data

(63) Continuation of application No. 13/619,531, filed on Sep. 14, 2012, now abandoned.

(51) Int. Cl.
*A61B 5/02* (2006.01)
*A61B 5/00* (2006.01)
(Continued)

(52) U.S. Cl.
CPC ...... *A61B 5/02028* (2013.01); *A61B 5/02416* (2013.01); *A61B 5/02438* (2013.01);
(Continued)

(58) Field of Classification Search
CPC ............ A61B 5/02028; A61B 5/02416; A61B 5/02438; A61B 5/0402; A61B 5/7235;
(Continued)

(56) References Cited

U.S. PATENT DOCUMENTS

| 4,094,308 | A | 6/1978 | Cormier |
| 4,282,655 | A | 8/1981 | Tinman |

(Continued)

FOREIGN PATENT DOCUMENTS

| EP | 0537383 A1 | 4/1993 |
| EP | 0841034 A1 | 5/1998 |

(Continued)

OTHER PUBLICATIONS

International Search Report and Written Opinion of the International Searching Authority for counterpart PCT application PCT/US2013/059922.

(Continued)

*Primary Examiner* — Amelie R Davis
(74) *Attorney, Agent, or Firm* — Shumaker & Sieffert, P.A.

(57) ABSTRACT

A PPG system includes a processor configured to receive a PPG signal from a PPG sensor, the PPG signal having a plurality of pulses each representing a heartbeat of a patient. The processor is also configured to determine an amplitude variance of the plurality of pulses over a time period, determine a pulse period variance of the PPG signal over the time period, determine a cardiac stability based on a ratio of the amplitude variance and the pulse period variance, and provide an indication of the cardiac stability via a display. The amplitude variance includes an average of squared differences of an amplitude of a peak of each pulse of the plurality of pulses from a mean amplitude of the plurality of pulses over the time period, and the mean amplitude includes an average of respective midpoints of each of the plurality of pulses over the time period.

22 Claims, 7 Drawing Sheets

(51) Int. Cl.
  *A61B 5/024* (2006.01)
  *A61B 5/318* (2021.01)
  *A61B 7/04* (2006.01)
  *A61B 8/02* (2006.01)

(52) U.S. Cl.
  CPC ............ *A61B 5/318* (2021.01); *A61B 5/7235* (2013.01); *A61B 5/742* (2013.01); *A61B 5/746* (2013.01); *A61B 7/04* (2013.01); *A61B 8/02* (2013.01)

(58) Field of Classification Search
  CPC ........... A61B 5/742; A61B 5/746; A61B 7/04; A61B 8/02
  See application file for complete search history.

(56) References Cited

U.S. PATENT DOCUMENTS

| | | | |
|---|---|---|---|
| 4,289,141 A | 9/1981 | Cormier | |
| 4,450,527 A | 5/1984 | Sramek | |
| 4,788,982 A * | 12/1988 | Gedeon | A61B 5/02416 600/479 |
| 5,092,339 A | 3/1992 | Geddes et al. | |
| 5,178,151 A | 1/1993 | Sackner | |
| 5,275,159 A | 1/1994 | Griebel | |
| 5,331,960 A | 7/1994 | Krenzke | |
| 5,408,327 A | 4/1995 | Geiler et al. | |
| 5,445,160 A * | 8/1995 | Culver | A61B 5/0836 128/205.23 |
| 5,595,182 A | 1/1997 | Krivitski | |
| 5,743,268 A | 4/1998 | Kabal | |
| 5,817,010 A | 10/1998 | Hibl | |
| 5,833,618 A | 11/1998 | Caro et al. | |
| 5,913,826 A | 6/1999 | Blank | |
| 5,935,066 A | 8/1999 | Harris | |
| 6,004,272 A | 12/1999 | Barry et al. | |
| 6,045,509 A | 4/2000 | Caro et al. | |
| 6,155,984 A | 12/2000 | Krivitski | |
| 6,292,686 B1 | 9/2001 | Chaiken et al. | |
| 6,371,921 B1 | 4/2002 | Caro et al. | |
| 6,389,306 B1 | 5/2002 | Chaiken et al. | |
| 6,503,206 B1 | 1/2003 | Li et al. | |
| 6,565,513 B1 | 5/2003 | Phillips | |
| 6,616,613 B1 | 9/2003 | Goodman | |
| 6,645,155 B2 | 11/2003 | Inukai et al. | |
| 6,716,177 B2 | 4/2004 | Nomura | |
| 6,719,705 B2 | 4/2004 | Mills | |
| 6,740,072 B2 | 5/2004 | Starkweather et al. | |
| 6,754,523 B2 | 6/2004 | Toole | |
| 6,758,822 B2 | 7/2004 | Romano | |
| 6,760,608 B2 | 7/2004 | Lynn | |
| 6,776,764 B2 | 8/2004 | Pinsky | |
| 6,816,266 B2 | 11/2004 | Varshneya et al. | |
| 6,869,402 B2 | 3/2005 | Arnold | |
| 6,875,176 B2 | 4/2005 | Mourad et al. | |
| 7,022,077 B2 | 4/2006 | Mourad et al. | |
| 7,033,320 B2 | 4/2006 | Von Behren et al. | |
| 7,056,292 B2 | 6/2006 | Hutchinson | |
| 7,123,953 B2 | 10/2006 | Starobin et al. | |
| 7,171,271 B2 | 1/2007 | Koh et al. | |
| 7,194,293 B2 | 3/2007 | Baker, Jr. | |
| 7,220,230 B2 | 5/2007 | Roteliuk et al. | |
| 7,452,333 B2 | 11/2008 | Roteliuk | |
| 7,462,152 B2 | 12/2008 | Kolluri et al. | |
| 7,615,011 B2 | 11/2009 | Sugo et al. | |
| 7,674,231 B2 | 3/2010 | McCombie et al. | |
| 7,704,209 B2 | 4/2010 | Bennett et al. | |
| 7,747,301 B2 | 6/2010 | Cheng et al. | |
| 7,771,364 B2 | 8/2010 | Arbel et al. | |
| 7,785,263 B2 | 8/2010 | Roteliuk et al. | |
| 7,806,830 B2 | 10/2010 | Bernstein | |
| 7,850,617 B2 | 12/2010 | Goedje et al. | |
| 7,881,762 B2 | 2/2011 | Kling et al. | |
| 7,894,869 B2 | 2/2011 | Hoarau | |
| 7,899,510 B2 | 3/2011 | Hoarau | |
| 7,976,472 B2 | 7/2011 | Kiani | |
| 8,073,516 B2 | 12/2011 | Scharf et al. | |
| 8,073,518 B2 | 12/2011 | Chin | |
| 8,187,197 B2 | 5/2012 | Shapira et al. | |
| 8,211,031 B2 | 7/2012 | Poupko et al. | |
| 2002/0022785 A1 | 2/2002 | Romano | |
| 2002/0082485 A1 | 6/2002 | Faithfull et al. | |
| 2002/0193692 A1 | 12/2002 | Inukai et al. | |
| 2003/0130586 A1 | 7/2003 | Starobin et al. | |
| 2003/0153838 A1 | 8/2003 | Nomura | |
| 2003/0167012 A1 | 9/2003 | Friedman et al. | |
| 2004/0162499 A1 | 8/2004 | Nagai et al. | |
| 2005/0080345 A1 | 4/2005 | Finburgh et al. | |
| 2005/0085707 A1 | 4/2005 | Korsten et al. | |
| 2005/0124903 A1 | 6/2005 | Roteliuk et al. | |
| 2005/0197549 A1 | 9/2005 | Baker, Jr. | |
| 2005/0240087 A1 | 10/2005 | Keenan et al. | |
| 2006/0009700 A1 | 1/2006 | Brumfield et al. | |
| 2006/0184051 A1 | 8/2006 | Hempstead et al. | |
| 2006/0224053 A1 | 10/2006 | Black et al. | |
| 2007/0093702 A1 | 4/2007 | Yu et al. | |
| 2007/0213625 A1 | 9/2007 | Nayak et al. | |
| 2007/0249949 A1 | 10/2007 | Hadley | |
| 2008/0082004 A1 | 4/2008 | Banet et al. | |
| 2008/0119329 A1 | 5/2008 | Punkka et al. | |
| 2008/0139958 A1 | 6/2008 | Uemura et al. | |
| 2008/0183232 A1 | 7/2008 | Voss et al. | |
| 2008/0287815 A1 | 11/2008 | Chon et al. | |
| 2009/0076399 A1 | 3/2009 | Arbel et al. | |
| 2009/0099459 A1 | 4/2009 | Svanberg et al. | |
| 2009/0149762 A1 | 6/2009 | Ou Yang et al. | |
| 2009/0177110 A1 | 7/2009 | Lyden et al. | |
| 2009/0198140 A1 | 8/2009 | Riobo Aboy et al. | |
| 2009/0204012 A1 | 8/2009 | Joeken | |
| 2009/0240119 A1 | 9/2009 | Schwaibold et al. | |
| 2009/0326353 A1 | 12/2009 | Watson et al. | |
| 2009/0326388 A1 | 12/2009 | Watson et al. | |
| 2009/0326395 A1 | 12/2009 | Watson | |
| 2010/0016739 A1 | 1/2010 | Shelley et al. | |
| 2010/0049007 A1 | 2/2010 | Sterling et al. | |
| 2010/0049071 A1 | 2/2010 | Goor et al. | |
| 2010/0081895 A1 | 4/2010 | Zand | |
| 2010/0152547 A1 | 6/2010 | Sterling et al. | |
| 2010/0152591 A1 | 6/2010 | Yu et al. | |
| 2010/0160794 A1 | 6/2010 | Banet et al. | |
| 2010/0191128 A1 | 7/2010 | Shelley et al. | |
| 2010/0210924 A1 | 8/2010 | Parthasarathy et al. | |
| 2010/0249542 A1 | 9/2010 | Thijs et al. | |
| 2010/0249559 A1 | 9/2010 | Lovejoy | |
| 2010/0249612 A1 | 9/2010 | Cohen | |
| 2010/0268090 A1 | 10/2010 | Rubinstein et al. | |
| 2010/0268101 A1 | 10/2010 | Sugo | |
| 2010/0268518 A1 | 10/2010 | Sugo | |
| 2010/0298689 A1 | 11/2010 | Wang | |
| 2010/0324388 A1 | 12/2010 | Moon et al. | |
| 2010/0324431 A1 | 12/2010 | Addison et al. | |
| 2010/0324827 A1 | 12/2010 | Addison et al. | |
| 2010/0324849 A1 * | 12/2010 | Ueno | G06F 17/18 702/66 |
| 2011/0009754 A1 | 1/2011 | Wenzel et al. | |
| 2011/0009755 A1 | 1/2011 | Wenzel et al. | |
| 2011/0026784 A1 | 2/2011 | Van Slyke et al. | |
| 2011/0034813 A1 | 2/2011 | Cohen et al. | |
| 2011/0040345 A1 | 2/2011 | Wenzel et al. | |
| 2011/0060234 A1 | 3/2011 | Zhou et al. | |
| 2011/0060531 A1 | 3/2011 | Sugo et al. | |
| 2011/0077532 A1 | 3/2011 | Kim et al. | |
| 2011/0087115 A1 | 4/2011 | Sackner et al. | |
| 2011/0098112 A1 | 4/2011 | LeBoeuf et al. | |
| 2011/0098546 A1 | 4/2011 | Farazi et al. | |
| 2011/0105918 A1 | 5/2011 | Fortin et al. | |
| 2011/0172504 A1 | 7/2011 | Wegerich | |
| 2011/0209915 A1 | 9/2011 | Telfort et al. | |
| 2011/0224564 A1 | 9/2011 | Moon et al. | |
| 2011/0270097 A1 | 11/2011 | Aboy et al. | |
| 2011/0301436 A1 | 12/2011 | Teixeira | |
| 2012/0022350 A1 | 1/2012 | Teixeira | |
| 2012/0029320 A1 | 2/2012 | Watson et al. | |

(56) References Cited

U.S. PATENT DOCUMENTS

| | | |
|---|---|---|
| 2012/0029361 A1 | 2/2012 | Addison et al. |
| 2012/0029363 A1 | 2/2012 | Lund |
| 2012/0046557 A1 | 2/2012 | Kiani |
| 2012/0053433 A1 | 3/2012 | Chamoun et al. |
| 2012/0053469 A1 | 3/2012 | Melker |
| 2012/0065485 A1 | 3/2012 | Benni et al. |
| 2012/0065527 A1 | 3/2012 | Gill et al. |
| 2012/0065528 A1 | 3/2012 | Gill et al. |
| 2012/0078069 A1 | 3/2012 | Melker |
| 2012/0109018 A1 | 5/2012 | Gertner et al. |
| 2012/0136261 A1 | 5/2012 | Sethi et al. |
| 2012/0172723 A1 | 7/2012 | Gertner |
| 2012/0172732 A1 | 7/2012 | Meyer, Jr. |
| 2013/0035738 A1* | 2/2013 | Karst ............ A61N 1/36507 607/25 |
| 2014/0081152 A1* | 3/2014 | Clinton ............ A61B 5/7235 600/479 |

FOREIGN PATENT DOCUMENTS

| | | |
|---|---|---|
| EP | 1443856 A2 | 8/2004 |
| EP | 1769737 A1 | 4/2007 |
| EP | 1884189 A1 | 2/2008 |
| EP | 2047794 A1 | 4/2009 |
| EP | 2217140 A1 | 8/2010 |
| EP | 2281508 A1 | 2/2011 |
| WO | 1991/13589 A1 | 9/1991 |
| WO | 1994/14372 A1 | 7/1994 |
| WO | 1997/47236 A1 | 12/1997 |
| WO | 1998/41279 A1 | 9/1998 |
| WO | 2002/03076 A2 | 1/2002 |
| WO | 2003/082099 A1 | 10/2003 |
| WO | 2004/071292 A1 | 8/2004 |
| WO | 2005/055825 A1 | 6/2005 |
| WO | 2006/100676 A2 | 9/2006 |
| WO | 2007/109065 A1 | 9/2007 |
| WO | 2008/094598 A2 | 8/2008 |
| WO | 2008/144404 A1 | 11/2008 |
| WO | 2008/144525 A1 | 11/2008 |
| WO | 2009/009761 A1 | 1/2009 |
| WO | 2009/014420 A1 | 1/2009 |
| WO | 2009/101140 A1 | 8/2009 |
| WO | 2010/001231 A2 | 1/2010 |
| WO | 2010/045556 A2 | 4/2010 |
| WO | 2010/096475 A1 | 8/2010 |
| WO | 2010/111073 A1 | 9/2010 |
| WO | 2010/124034 A2 | 10/2010 |
| WO | 2010/146326 A1 | 12/2010 |
| WO | 2010/146327 A1 | 12/2010 |
| WO | 2011/047211 A1 | 4/2011 |
| WO | 2011/050066 A2 | 4/2011 |
| WO | 2011/051822 A1 | 5/2011 |
| WO | 2011/060220 A1 | 5/2011 |
| WO | 2011/077294 A1 | 6/2011 |
| WO | 2011/080190 A1 | 7/2011 |
| WO | 2011/080194 A1 | 7/2011 |
| WO | 2011/087927 A1 | 7/2011 |
| WO | 2011/089488 A1 | 7/2011 |
| WO | 2012/009350 A1 | 1/2012 |
| WO | 2012/014065 A1 | 2/2012 |
| WO | 2012/015426 A1 | 2/2012 |
| WO | 2012/027613 A1 | 3/2012 |
| WO | 2012/032413 A2 | 3/2012 |
| WO | 2012/032536 A2 | 3/2012 |
| WO | 2012/052926 A2 | 4/2012 |
| WO | 2012/075322 A2 | 6/2012 |
| WO | 2012/076957 A1 | 6/2012 |

OTHER PUBLICATIONS

Leahy, Martin J., et al.; "Sensor Validation in Biomedical Applications," IFAC Modelling and Control in Biomedical Systems, Warwick, UK; pp. 221-226 (1997).

Barreto, Armando B., et al.; "Adaptive LMS Delay Measurement in dual Blood Volume Pulse Signals for Non-Invasive Monitoring," IEEE, pp. 117-120 (1997).

East, Christine E., et al.; "Fetal Oxygen Saturation and Uterine Contractions During Labor," American Journal of Perinatology, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," Proceedings of the 20th Annual International conference of the IEEE Engie in Medicine and Biology Society, vol. 20, No. 6, pp. 3072-3075, 1998.

Such, Hans Olaf; "Optoelectronic Non-invasive Vascular Diagnostics Using multiple Wavelength and Imaging Approach," Dissertation, (1998).

Todd, Bryan, et al.; "The Identification of Peaks in Physiological Signals," Computers and Biomedical Research, vol. 32, pp. 322-335 (1999).

Goldman, Julian M.; "Masimo Signal Extraction Pulse Oximetry," Journal of Clinical Monitoring and Computing, vol. 16, pp. 475-483 (2000).

Coetzee, Frans M.; "Noise-Resistant Pulse Oximetry Using a Synthetic Reference Signal," IEEE Transactions on Biomedical Engineering, vol. 47, No. 8, Aug. 2000, pp. 1018-1026.

Kaestle, S.; "Determining Artefact Sensitivity of New Pulse Oximeters in Laboratory Using Signals Obtained from Patient," Biomedizinische Technik, vol. 45 (2000).

Cysewska-Sobusaik, Anna; "Metrological Problems With noninvasive Transillumination of Living Tissues," Proceedings of SPIE, vol. 4515, pp. 15-24 (2001).

Belal, Suliman Yousef, et al.; "A fuzzy system for detecting distorted plethysmogram pulses in neonates and paediatric patients," Physiol. Meas., vol. 22, pp. 397-412 (2001).

Chan, K.W., et al.; "17.3: Adaptive Reduction of Motion Artifact from Photoplethysmographic Recordings using a Variable Step-Size LMS Filter," IEEE, pp. 1343-1346 (2002).

Cyrill, D., et al.; "Adaptive Comb Filter for Quasi-Periodic Physiologic Signals," Proceedings of the 25th Annual International Conference of the IEEE EMBS, Cancun, Mexico, Sep. 17-21, 2003; pp. 2439-2442.

Stetson, Paul F.; "Determining Heart Rate from Noisey Pulse Oximeter Signals Using Fuzzy Logic," The IEEE International Conference on Fuzzy Systems, St. Louis, Missouri, May 25-28, 2003; pp. 1053-1058.

Lee, C.M., et al.; "Reduction of motion artifacts from photoplethysmographic recordings using wavelet denoising approach," IEEE EMBS Asian-Pacific Conference on Biomedical Engineering, Oct. 20-22, 2003; pp. 194-195.

Johansson, A.; "Neural network for photoplethysmographic respiratory rate monitoring," Medical & Biological Engineering & Computing, vol. 41, pp. 242-248 (2003).

Addison, Paul S., et al.; "A novel time-frequency-based 3D Lissajous figure method and its application to the determination of oxygen saturation from the photoplethysmogram," Institute of Physic Publishing, Meas. Sci. Technol., vol. 15, pp. L15-L18 (2004).

Huang, J., et al.; "Low Power Motion Tolerant Pulse Oximetry," Anesthesia & Analgesia 2002 94: S103.

Hamilton, Patrick S., et al.; "Effect of Adaptive Motion-Artifact Reduction on QRS Detection," Biomedical Instrumentation & Technology, pp. 197-202 (May-Jun. 2000).

Kim, J.M., et al.; "Signal Processing Using Fourier & Wavelet Transform for pulse oximetry," pp. II-310-II-311 (2001).

Odagiri, Y.; "Pulse Wave Measuring Device," Micromechatronics, vol. 42, No. 3, pp. 6-11 (published Sep. 1998) (Article in Japanese—contains English summary of article).

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Relente, A.R., et al.; "Characterization and Adaptive Filtering of Motion Artifacts in Pulse Oximetry using Accelerometers," Proceedings of the Second joint EMBS/BMES Conference, Houston, Texas, Oct. 23-26, 2002; pp. 1769-1770.

(56) References Cited

OTHER PUBLICATIONS

Neumann, R., et al.; "Fourier Artifact suppression Technology Provides Reliable SpO2,," Anesthesia & Analgesia 2002, 94: S105.
Gesquiere, Michael J., et al., "Impact of withdrawal of 450 ML of blook on respiration-induced oscillations of the ear plethysmographic waveform," Journal of Clinical Monitoring and Computing (2007) 21:277-282.
Wu, Dongmei, et al.; "Na*/H* Exchange inhibition delays the onset of hypovolemic circulatory shock in pigs," Shock, vol. 29, No. 4, pp. 519-525 (2008).
Chen, Liangyou, et al.; "IS respiration-induced variation in the photoplethysmogram associated with major hypovolemia in patients with actue tramatic injuries," Shock, vol. 34, No. 5, pp. 455-460 (2010).
McGrath, S.P., et al.; "Pulse oximeter plethysmographic waveform changes in awake, spontaneously breathing, hypovolemic volunteers," Anesth. Analg. vol. 112 No. 2, pp. 368-374 (2010).
Shamir, M., et al.; "Pulse oximetry plethysmographic waveform during changes in blood volume," British Journal of Anaesthesia 82(2): 178-81 (1999).
"A Computer Based Photoplethysmographic Vascular Analyzer Through Derivatives," Gonzalez, et al, Computers in Cardiology (2008). (Applicant points out, in accordance with MPEP 609.04(a), that the year of publication, 2008, is sufficiently earlier than the effective U.S. filing date, so that the particular month of publication is not in issue.).
"Derivation of Respiratory Signals from Multi-lead ECGS, Moody," et al. (1985). (Applicant points out, in accordance with MPEP 609.04(a), that the year of publication, 1985 is sufficiently earlier than the effective U.S. filing date, so that the particular month of publication is not in issue.).
"Flow dependent photothermal modulation of the photacoustic response," Sheinfeld, et al, Photonos Plus Ultrasound: Imaging and Sensing (2012) (Applicant points out, in accordance with MPEP 609.04(a), that the year of publication, 2012, is sufficiently earlier than the effective U.S. filing date, so that the particular month of publication is not in issue.).
"How to measure heart rate?" Vogel, et al. Eur. J. Clin Paramacol (2004) 60.461-466 (Applicant points out, in accordance with MPEP 609.04(a), that the year of publication, 2004, is sufficiently earlier than the effective U.S. filing date, so that the particular month of publication is not in issue.).
"Monitoring of Reactive Hyperemia Using Photoplethysmographic Pulse Amplitude and Transit Time," Selvavaj, et al. Journal of Clinical Monitoring and Computing 23:315-322 (2009). (Applicant points out, in accordance with MPEP 609.04(a), that the year of publication, 2009, is sufficiently earlier than the effective U.S. filing date, so that the particular month of publication is not in issue.).
"Near-Infrared Spectrometry (NIRS) and Venous-side Monitoring of the Circulation," Hoffman (2011). (Applicant points out, in accordance with MPEP 609.04(a), that the year of publication, 2011, is sufficiently earlier than the effective U.S. filing date, so that the particular month of publication is not in issue.).
"Non-constrained Blood Pressure Monitoring Using ECG and PPG for Personal Healthcare," Yoon, et al, (2008). (Applicant points out, in accordance with MPEP 609.04(a), that the year of publication, 2008, is sufficiently earlier than the effective U.S. filing date, so that the particular month of publication is not in issue.).
"Noninvasive Assessment of the Digital Volume Pulse: Comparison with the Peripheral Pressure Pulse," Millasseau, et al., Journal of the American Heart Association (2000). (Applicant points out, in accordance with MPEP 609.04(a), that the year of publication, 2000, is sufficiently earlier than the effective U.S. filing date, so that the particular month of publication is not in issue.).
"Non-Invasive Estimation of Cardiac Output from Finger Photoplethysmogram Based on Windkessel Model," Peon, Bulletin of Advance Technology Research, vol. 4, No. 6 (2010). (Applicant points out, in accordance with MPEP 609.04(a), that the year of publication, 2010, is sufficiently earlier than the effective U.S. filing date, so that the particular month of publication is not in issue.).
"On the Analysis of Fingertip Photoplethysmogram Signals," Elgendi, Current Cardiology Reviews, 2012. (Applicant points out, in accordance with MPEP 609.04(a), that the year of publication, 2012, is sufficiently earlier than the effective U.S. filing date, so that the particular month of publication is not in issue.).
"Photoacoustic thermal diffusion flowmetry," Sheinfeld, et al., Biomedical Optics Express vol. 3, No. 4 (2012) Applicant points out, in accordance with MPEP 609.04(a), that the year of publication, 2012, is sufficiently earlier than the effective U.S. filing date, so that the particular month of publication is not in issue.).
"Photoplethsmography and its application in clinical physiological measurement," Physiol. Meas. 28 (2007). (Applicant points out, in accordance with MPEP 609.04(a), that the year of publication, 2007, is sufficiently earlier than the effective U.S. filing date, so that the particular month of publication is not in issue.).
"Pulse oximeter plethysmograph variation and its relationship to the arterial waveform in mechanically ventilated childer," Chandler, et al. J. Clin. Manit. Comput. (2012). (Applicant points out, in accordance with MPEP 609.04(a), that the year of publication, 2012, is sufficiently earlier than the effective U.S. filing date, so that the particular month of publication is not in issue.).
"Relation between repiratory variations in pulse oximetry plethysmographic waveform amplitude and arterial pulse pressure in ventilated patients," Cannesson, et al. Ciritical Care (2005). (Applicant points out, in accordance with MPEP 609.04(a), that the year of publication, 2005, is sufficiently earlier than the effective U.S. filing date, so that the particular month of publication is not in issue.).
"Resting Heart Rate in Cardiovascular Disease," Fox, et al. Journal of the Amercan College of Cardiology vol. 50, No. 9 (2007). (Applicant points out, in accordance with MPEP 609.04(a), that the year of publication, 2007, is sufficiently earlier than the effective U.S. filing date, so that the particular month of publication is not in issue.).
"The shape and dimensions of photoplethsymographic pulse waves; a measurement repeatability study," Marcinkevics, et al. Acta Universitatis Latviensis,vol. 753, Bilology, pp. 99-106 (2009). (Applicant points out, in accordance with MPEP 609.04(a), that the year of publication, 2009, is sufficiently earlier than the effective U.S. filing date, so that the particular month of publication is not in issue.).
"Variations in Arterial Blood Pressure and Photoplethysmography During Mechanical Ventilation," Natalani, et al., Techology, Computing, and Simulation, vol. 103, No. 5, (2006). (Applicant points out, in accordance with MPEP 609.04(a), that the year of publication, 2006, is sufficiently earlier than the effective U.S. filing date, so that the particular month of publication is not in issue.).
"Venus Oximetry," Signa Vitae 2007. (Applicant points out, in accordance with MPEP 609.04(a), that the year of publication, 2007, is sufficiently earlier than the effective U.S. filing date, so that the particular month of publication is not in issue.).
"Why measure resting heart rate?" Nauman (2012). (Applicant points out, in accordance with MPEP 609.04(a), that the year of publication, 2012, is sufficiently earlier than the effective U.S. filing date, so that the particular month of publication is not in issue.).
Prosecution History from U.S. Appl. No. 13/619,531, dated Sep. 17, 2012 through Jun. 19, 2015, 149 pp.

* cited by examiner

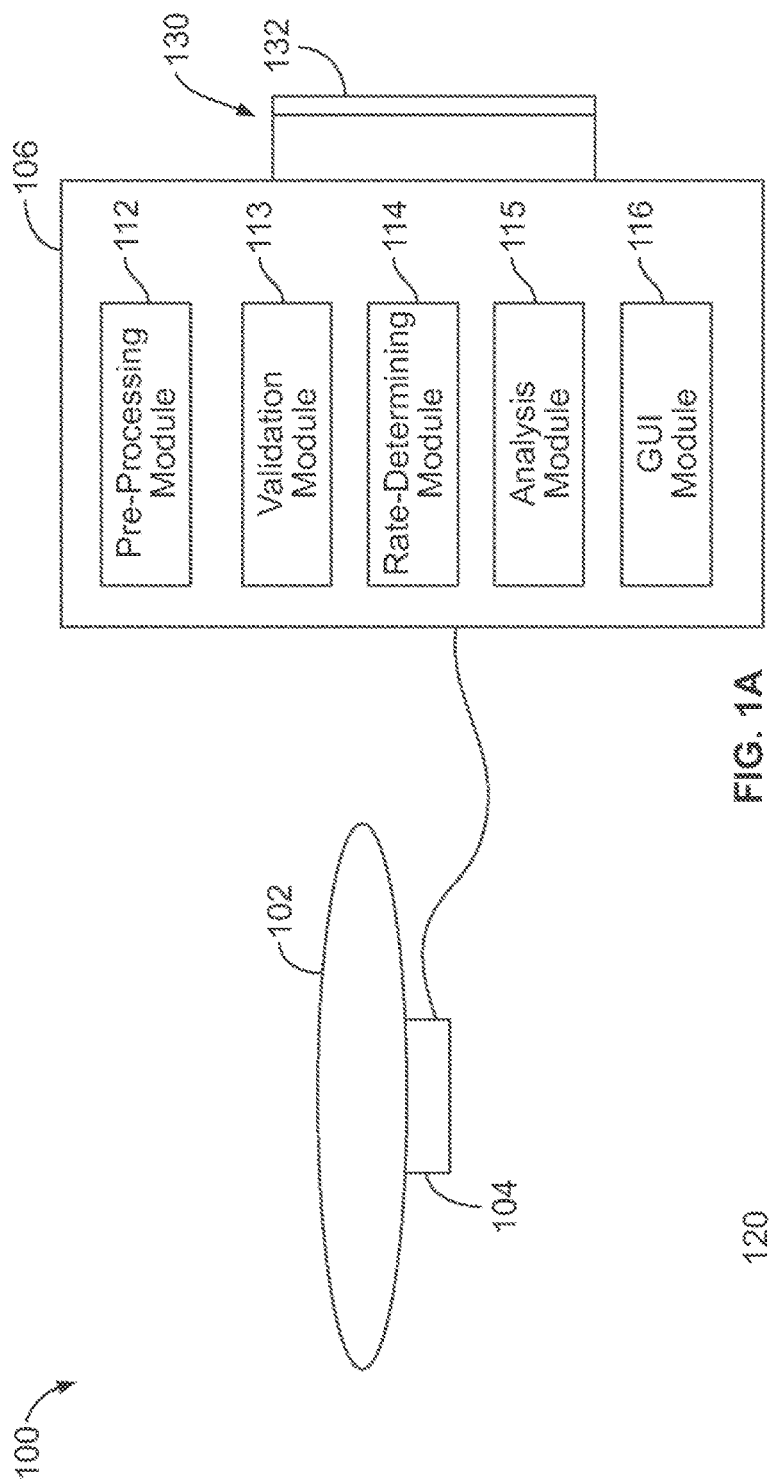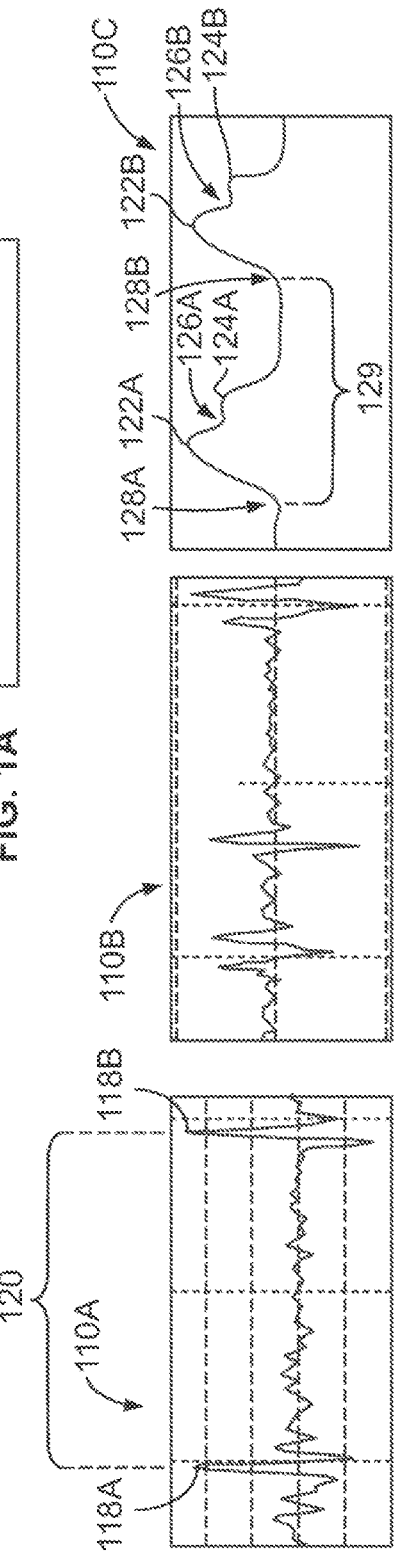

SYSTEM AND METHOD FOR DETERMINING STABILITY OF CARDIAC OUTPUT

CROSS-REFERENCE TO RELATED APPLICATION

This application is a continuation of U.S. application Ser. No. 13/619,531, filed Sep. 14, 2012, entitled "System and Method for Determining Stability of Cardiac Output," the disclosure of which is hereby incorporated by reference in its entirety.

BACKGROUND

Embodiments of the present disclosure generally relate to physiological signal processing and, more particularly, to processing physiological signals to determine a cardiac stability ratio of a patient.

In cardiovascular physiology, cardiac output (CO) and stroke volume (SV) are important measurements of cardiac strength and stability. Because SV and CO decreases in certain conditions and disease states, SV and CO correlate with cardiac function. CO is the volume of blood being pumped by the heart and is a product of SV and the heart rate of the patient.

SV has traditionally been calculated using measurements of ventricle volumes from an echocardiogram (ECG) and subtracting the volume of the blood in the ventricle at the end of a beat (end-systolic volume) from the volume of blood just prior to the beat (called end-diastolic volume). Some systems and methods have been used to measure stroke volume using a photoplethysmogram (PPG) system in connection with ECG systems to aid in determining SV by measuring pulse transit times from the pulse measurement by the ECG system and the pulse measurement by the PPG system. The PPG system performs a non-invasive, optical measurement that may be used to detect changes in blood volume within tissue, such as skin, of an individual.

SUMMARY

Certain embodiments provide a PPG system for determining cardiac stability of a patient. The PPG system may include a PPG sensor configured to be secured to an anatomical portion of the patient. The PPG sensor is configured to sense a physiological characteristic of the patient. The PPG system may include a monitor operatively connected to the PPG sensor. The monitor may receive a PPG signal from the PPG sensor. The monitor includes a cardiac stability analysis module configured to determine an amplitude variance of the PPG signal over a predetermined time period and configured to determine a pulse period variance of the PPG signal over the time period. The cardiac stability analysis module is configured to determine cardiac stability as a function of the amplitude variance and the pulse period variance. The cardiac stability analysis module may determine a cardiac stability ratio as an amplitude variance over the pulse period variance.

Optionally, in other embodiments, the cardiac stability may be calculated as a function of the pulse period variance and as a function of an inverse of an amplitude variance. The cardiac stability analysis module may determine a cardiac stability ratio as an inverse variance of the amplitude over the pulse period variance.

The cardiac stability analysis module may calculate the cardiac stability as a product of the cardiac stability ratio and a scaling factor. Optionally, a numerator of the cardiac stability ratio may be configured to decrease as the cardiac stability of the patient decreases and the denominator of the cardiac stability ratio may be configured to increase as the cardiac stability of the patient decreases. The cardiac stability ratio may be configured to decrease as the cardiac stability of the patient decreases.

Optionally, the cardiac stability analysis module may determine the amplitude variance as an average of the squared differences of each of the amplitudes from the mean amplitude over the time period. The cardiac stability analysis module may determine the pulse period variance as an average of the squared differences of each of the pulse periods from the mean pulse period over the time period.

The PPG signal may form a PPG waveform. The cardiac stability analysis module may analyze a contour of the PPG waveform along the primary peak to identify a minimum amplitude and a maximum amplitude for each pulse. The cardiac stability analysis module may calculate the amplitude variance based on the absolute amplitude of each pulse.

Optionally, the monitor may include an alarm. The monitor may store a threshold cardiac stability. The monitor may activate the alarm when the determined cardiac stability crosses the threshold cardiac stability. The monitor may display an output of the cardiac stability on a display.

Certain embodiments provide a method of determining cardiac stability of a patient from a PPG system. The method includes securing a PPG sensor to an anatomical portion of the patient and sensing a physiological characteristic of the patient with the PPG sensor. The method includes receiving a PPG signal from the sensor at a monitor that includes a cardiac stability analysis module. The method includes analyzing an amplitude component of the PPG signal at the cardiac stability analysis module to determine an amplitude variance of the PPG signal over a predetermined time period. The method includes analyzing a temporal component of the PPG signal at the cardiac stability analysis module to determine a pulse period variance of the PPG signal over the time period. The method includes calculating cardiac stability of the patient at the cardiac stability analysis module based on the amplitude variance and the pulse period variance.

Certain embodiments provide a tangible and non-transitory computer readable medium that includes one or more sets of instructions configured to direct a computer to receive a PPG signal from a sensor secured to an anatomical portion of a patient over a predetermined time period, determine an amplitude variance of the PPG signal over the time period, determine a pulse period variance of the PPG signal over the time period, and calculate cardiac stability of the patient based on the amplitude variance and the pulse period variance.

Embodiments of the present disclosure allow for quick and simple determination of cardiac stability through analysis of a PPG signal. In contrast to previous systems and methods, embodiments may not require an ECG system to determine cardiac stability. The PPG signal may be obtained from a single pleth-only system. The cardiac stability may be determined quickly, frequently, inexpensively, with little power, and with high sensitivity.

Certain embodiments may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

BRIEF DESCRIPTION OF THE DRAWINGS

FIG. 1A illustrates a simplified block diagram of a system configured to determine a physiological parameter of a patient, according to an embodiment.

FIG. 1B illustrates an electrocardiogram (ECG) waveform of the patient, according to an embodiment.

FIG. 1C illustrates a phonocardiogram (PCG) waveform of the patient, according to an embodiment.

FIG. 1D illustrates a photoplethysmogram (PPG) waveform of the patient, according to an embodiment.

DETAILED DESCRIPTION

Figure 2:
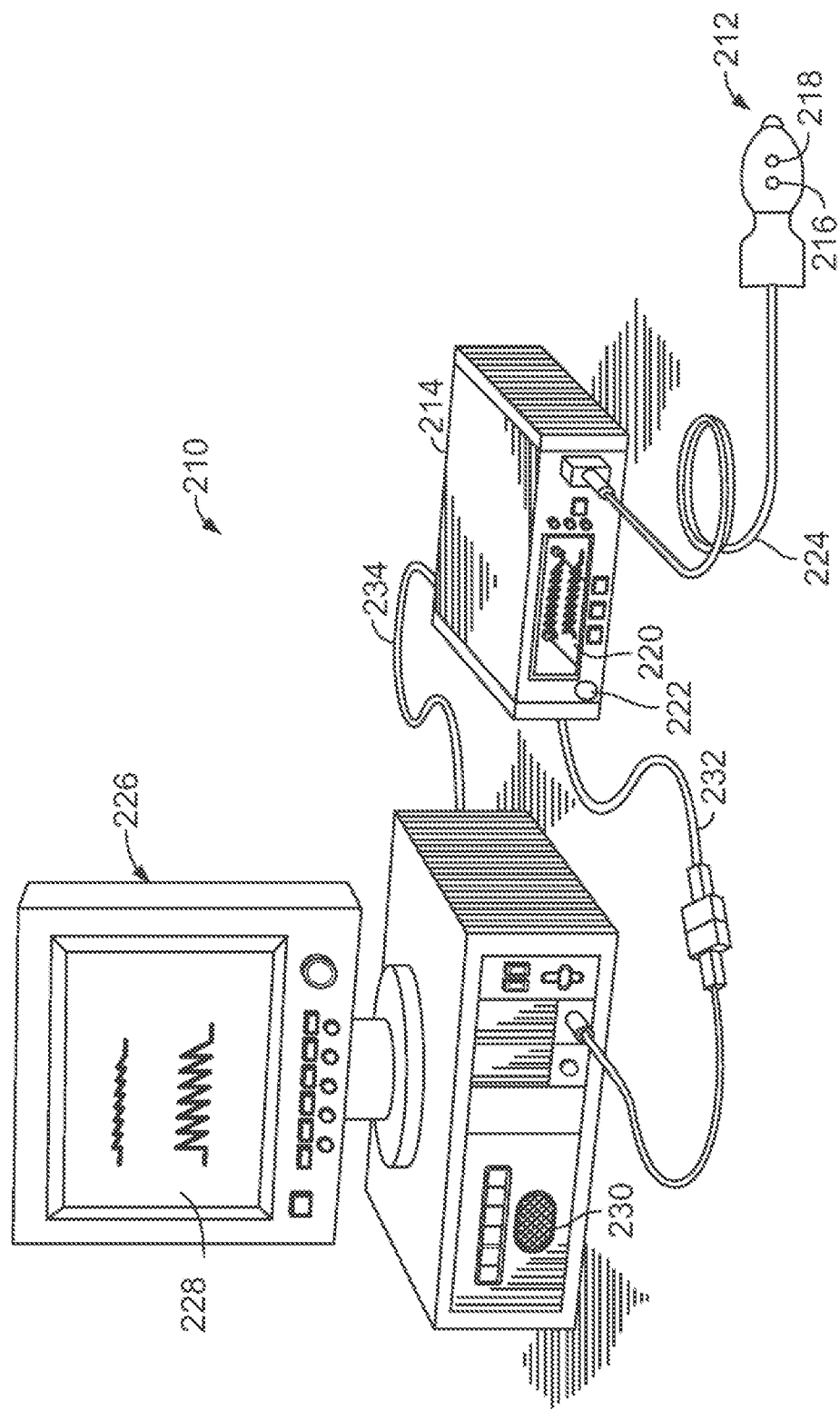
FIG. 2 illustrates an isometric view of a PPG system, according to an embodiment.

FIG. 1A illustrates a simplified block diagram of a system 100 configured to determine a physiological parameter of a patient 102. The system 100 is configured to acquire physiological signals (or biosignals) from the patient 102 and analyze the physiological signals to determine cardiac stability of the patient. The cardiac stability may be based on a physiological parameter determined by the system 100, such as a heart rate (HR), a blood pressure (BP), a stroke volume (SV) and/or a cardiac output (CO) of the patient 102. The physiological signals are indicative of phenomena occurring in the patient. For example, the physiological signals may describe cardiac function relating to cardiac strength and patient safety. The system 100 may provide a sensitive indicator of cardiac stability and may relate to hypovolemia or other conditions. The physiological signals may be electrical, optical, and/or acoustical signals.

The system 100 may include a sensor 104 that is configured to detect one or more types of physiological signals. By way of example, the system 100 may include an electrocardiogram (ECG) system that detects electrical signals corresponding to muscle excitation of the heart. In such cases, the sensor 104 may include a plurality of electrodes that are coupled to different anatomical locations of the patient 102 (e.g., chest, wrists, and/or ankles). FIG. 1B illustrates, according to an embodiment, a representative ECG waveform 110A based on the ECG signals acquired by the electrode-sensor 104.

As another example, the system 100 may include a phonocardiogram (PCG) system that detects sounds that may be caused by the closing of heart valves. In such cases, the sensor 104 may include one or more microphones that are coupled to the patient 102. FIG. 1C illustrates, according to an embodiment, a representative PCG waveform 110B based on the PCG signals acquired by the microphone-sensor 104. In alternative embodiments, the system 100 includes an ultrasound system configured to detect heart beats from the patient 102.

In certain embodiments, the system 100 includes a photoplethysmogram (PPG) system, which can measure changes in blood volume through an anatomical portion or location (e.g., a finger). A typical example of a PPG system is a pulse oximetry system although other PPG systems exist and may be used with embodiments described herein. The PPG-sensor 104 may include a probe having one or more light sources and one or more light detectors that are coupled to the patient 102. The light source(s) provide an incident light that is scattered, absorbed, reflected, and/or transmitted by the blood. The light detector(s) detect an amount of light that may correspond to blood volume. For example, as the volume of blood increases at the anatomical location, the light is attenuated more and, as such, a smaller amount of light is detected. FIG. 1C illustrates, according to an embodiment, a representative PPG waveform 110C based on the PPG signals acquired by the PPG-sensor 104.

As shown in FIG. 1A, the system 100 may include a monitor (or computing system) 106 that includes one or more components for analyzing and/or processing the physiological signals. For example, the monitor 106 may include a pre-processing module 112, a validation module 113, a rate-determining module 114, an analysis module 115, and a graphical user interface (GUI) module 116. As used herein, a "module" may include hardware components (e.g., processor, controller), software components, or a combination thereof including any associated circuitry.

The pre-processing module 112 is configured to remove unwanted signal data (e.g., noise) from raw physiological signal data obtained from the individual 102. For example, raw PPG signals may include artifacts caused by motion of the patient relative to the light detector, instrumentation bias (e.g., bias by amplifiers used in the PPG system), power line interference, low amplitude PPG signals, etc. Raw physiological signals from other types of monitoring systems, such as ECG and PCG systems, may also include unwanted noise. The pre-processing module 112 is configured to remove the noise to provide clearer and/or cleaner physiological signals to the other components of the system 100. The validation module 113 is configured to analyze the physiological signals to identify valid heart beats and waveforms from the physiological signals. In some embodiments, the validation module 113 is part of the pre-processing module 112 or another module. The validation module 113 may analyze the physiological signals after the physiological signals have been processed. In some embodiments, the validation module 113 examines the physiological signals to identify one or more reference features in the physiological signals. For instance, a series of data points over time may provide waveforms, such as the waveforms 110A-110C. A reference feature may be an identifiable point, segment, or characteristic of the waveform (e.g., peak, trough (or foot), notch, amplitude, width, area, slope of a designated segment, threshold, etc.) that may be relied upon in analysis of the physiological signals. In many cases, a reference feature of a waveform corresponds to a known physiological activity (e.g., excitation of heart muscles, closure or opening of valves, maximum volume of blood at an anatomical location, etc.). The validation module 113 may examine the data points, or a select number of data points (e.g., a segment of the waveform), to confirm that the data points are caused by a designated event of a cardiac cycle and are not a result of noise or other unwanted event, such as when the sensor 104 is being adjusted. The data points associated with valid heart beats may then be used by a rate-determining module 114 to determine a heart rate signal. In some embodiments, the data points that are not identified as corresponding to heart beats may not be considered in subsequent analysis.

The rate-determining module 114 is configured to analyze the heart beats or, more specifically, the data points corresponding to the valid heart beats identified by the validation module 113 and determine a heart rate (HR) of the individual at a designated moment of time. For example, the HR may be calculated by analyzing time intervals or pulse periods between two or more heart beats or by analyzing portions of a waveform that correspond to a single heart beat. By way of example only, when analyzing the physiological signals, the rate-determining module 114 may identify one or more reference features (e.g., points, segments, and/or characteristics that correspond to a waveform) that may be used to calculate HR. For example, in the ECG waveform 110A, the rate-determining module 114 may identify an R-wave peak 118 in each heart beat. A pulse period 120 between the R-wave peaks 118A, 118B may be determined and divided by a unit of time to calculate the HR. For example, if the time interval is 0.90 seconds between the two R-wave peaks 118A, 118B, then the HR is 67 beats/minute. The system may calculate a variance of each heart beat or a series of heart beats to determine one or more physiological parameters of the patient. For example, a variance of one or more pulse periods 120 may be analyzed.

Corresponding to each heart beat, the PPG waveform 110C may include a systolic peak 122, a diastolic peak 124, and a dichrotic notch 126 that exists therebetween. In some cases, the diastolic peak is not a peak but instead a change in slope. To determine HR, the rate-determining module 114 may identify for each heart beat a reference point that exists at a foot 128 of the wave before the systolic peak 122. The HR may be determined in a similar manner as described above with respect to the ECG waveform by identifying a time interval or pulse period 129 between the foot 128A and the foot 128B. The system may calculate a variance of each heart beat or a series of heart beats to determine one or more physiological parameters of the patient. For example, a variance of one or more pulse periods 129 may be analyzed.

However, it should be noted that the above description is just exemplary and that many reference points and/or waveform segments may be analyzed and used in calculating a HR or other physiological parameter of an individual. Furthermore, the physiological signals may be processed in various manners to determine a HR. For example, a first derivative or second derivative of the PPG waveform may be used to locate certain reference data points in the PPG waveform. Such reference data points may be used for determining the pulse period, heart rate or for determining other physiological parameters.

As will be described in greater detail below, the analysis module 115 is configured to identify data points from the physiological signals. The signal data points may be a limited number of data points from a series of data points. For example, the signal data points may correspond to a peak data point, a trough data point, an amplitude of the waveform or a portion of the waveform, a change in amplitude, a variance in amplitude compared to other pulses, a segment of data points that correspond to a slope of the waveform, and the like. To calculate a physiological parameter, such as a cardiac stability ratio, the analysis module 115 may use one or more of the data points to calculate the physiological parameter.

The system 100 may also include a user interface 130 that includes a display 132. The user interface 130 may include hardware, firmware, software, or a combination thereof that enables a user to directly or indirectly control operation of the system 100 and the various components thereof. The display 132 is configured to display one or more images, such as one or more of the waveforms 110A-110C. The display 132 may also be configured to show a representation of the physiological parameter, for example, a number representing cardiac stability of the patient.

In some embodiments, the user interface 130 may also include one or more input devices (not shown), such as a physical keyboard, mouse, touchpad, and/or touch-sensitive display. The user interface 130 may be operatively connected to the GUI module 116 and receive instructions from the GUI module 116 to display designated images on the display 132. The user interface 130 may also include a printer or other device for providing (e.g. printing) a report. The user interface 130 may also include an alarm or alert system.

There are many medical conditions in which cardiac stability is relevant. For example, cardiac stability may be an indicator of blood loss. Hypovolemia may be identified by analyzing cardiac stability. Hypovolemia may be identified more quickly using the system 100, such as by providing a representation of cardiac stability on the display 132.

Detecting a change in the cardiac stability or other physiological parameter, such as SV, CO, HR and/or BP, can alert medical providers to potentially dangerous patient conditions. Analyzing and/or processing the physiological signals to provide a representation of cardiac stability on a display for a care provider may be more meaningful than merely monitoring BP and HR readings. A monitoring system that tracks and provides information relating to cardiac stability for a care provider and indicates a patient status in response to a cardiac stability ratio provides a tool in patient diagnosis and treatment. The present disclosure relates to systems and methods for determining a cardiac stability ratio, and more particularly, relates to analyzing a trending nature of a PPG waveform to determine cardiac stability to alert a care provider to a patient condition. For example, the present disclosure relates to systems and methods that analyze a cardiac stability ratio of amplitude variance over pulse period variance to determine if a heart function is steady or unsteady.

FIG. 2 illustrates an isometric view of a PPG system 210, according to an embodiment. While the system 210 is shown and described as a PPG system 210, the system may be various other types of physiological detection systems, such as an electrocardiogram system, a phonocardiogram system, and the like. The PPG system 210 may be used as part of the system 100 (shown in FIG. 1). The PPG system 210 may be a pulse oximetry system, for example. The system 210 may include a PPG sensor 212 and a PPG monitor 214. The PPG sensor 212 may include an emitter 216 configured to emit light into tissue of a patient. For example, the emitter 216 may be configured to emit light at two or more wavelengths into the tissue of the patient. The PPG sensor 212 may also include a detector 218 that is configured to detect the emitted light from the emitter 216 that emanates from the tissue after passing through the tissue.

The system 210 may include a plurality of sensors forming a sensor array in place of the PPG sensor 212. Each of the sensors of the sensor array may be a complementary metal oxide semiconductor (CMOS) sensor, for example. Alternatively, each sensor of the array may be a charged coupled device (CCD) sensor. In another embodiment, the sensor array may include a combination of CMOS and CCD sensors. The CCD sensor may include a photoactive region and a transmission region configured to receive and transmit, while the CMOS sensor may include an integrated circuit having an array of pixel sensors. Each pixel may include a photodetector and an active amplifier. The emitter 216 and the detector 218 may be configured to be located at opposite sides of a digit, such as a finger or toe, in which case the light that is emanating from the tissue passes completely through the digit. The emitter 216 and the detector 218 may be arranged so that light from the emitter 216 penetrates the tissue and is reflected by the tissue into the detector 218, such as a sensor designed to obtain pulse oximetry data.

The sensor 212 or sensor array may be operatively connected to and draw power from the monitor 214. Optionally, the sensor 212 may be wirelessly connected to the monitor 214 and include a battery or similar power supply (not shown). The monitor 214 may be configured to calculate physiological parameters based at least in part on data received from the sensor 212 relating to light emission and detection. Alternatively, the calculations may be performed by and within the sensor 212 and the result of the oximetry reading may be passed to the monitor 214. Additionally, the monitor 214 may include a display 220 configured to display the physiological parameters or other information about the system 210 and the patient. The monitor 214 may also include a speaker 222 configured to provide an audible sound that may be used in various other embodiments, such as for example, sounding an audible alarm in the event that physiological parameters are outside a predefined normal range.

The sensor 212, or the sensor array, may be communicatively coupled to the monitor 214 via a cable 224. Alternatively, a wireless transmission device (not shown) or the like may be used instead of, or in addition to, the cable 224.

The system 210 may also include a multi-parameter workstation 226 operatively connected to the monitor 214. The workstation 226 may be or include a computing sub-system 230, such as standard computer hardware. The computing sub-system 230 may include one or more modules and control units, such as processing devices that may include one or more microprocessors, microcontrollers, integrated circuits, memory, such as read-only and/or random access memory, and the like. The workstation 226 may include a display 228, such as a cathode ray tube display, a flat panel display, such as a liquid crystal display (LCD), light-emitting diode (LED) display, a plasma display, or any other type of monitor. The computing sub-system 230 of the workstation 226 may be configured to calculate physiological parameters and to show information from the monitor 214 and from other medical monitoring devices or systems (not shown) on the display 228. For example, the workstation 226 may be configured to display cardiac stability of the patient, SV information, CO information, an estimate of a patient's blood oxygen saturation generated by the monitor 214 (referred to as an SpO2 measurement), pulse rate information from the monitor 214 and blood pressure from a blood pressure monitor (not shown) on the display 228.

The monitor 214 may be communicatively coupled to the workstation 226 via a cable 232 and/or 234 that is coupled to a sensor input port or a digital communications port, respectively and/or may communicate wirelessly with the workstation 226. Alternatively, the monitor 214 and the workstation 226 may be integrated as part of a common device. Additionally, the monitor 214 and/or workstation 226 may be coupled to a network to enable the sharing of information with servers or other workstations. The monitor 214 may be powered by a battery or by a conventional power source such as a wall outlet.

Figure 3:
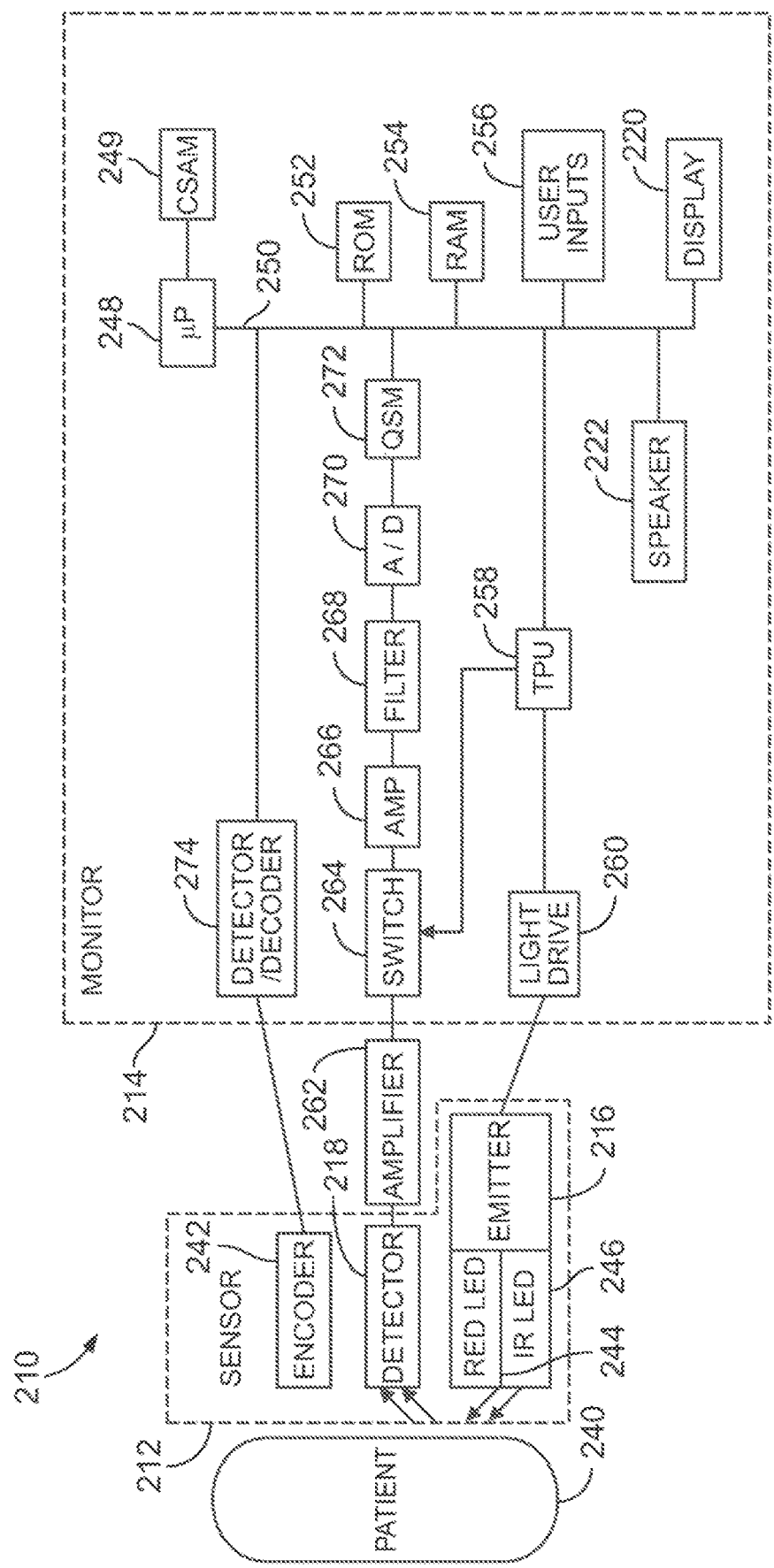
FIG. 3 illustrates a simplified block diagram of a PPG system, according to an embodiment.

FIG. 3 illustrates a simplified block diagram of the PPG system 210, according to an embodiment. When the PPG system 210 is a pulse oximetry system, the emitter 216 may be configured to emit at least two wavelengths of light (for example, red and infrared) into tissue 240 of a patient. Accordingly, the emitter 216 may include a red light-emitting light source such as a red light-emitting diode (LED) 244 and an infrared light-emitting light source such as an infrared LED 246 for emitting light into the tissue 240 at the wavelengths used to calculate the patient's physiological parameters. For example, the red wavelength may be between about 600 nm and about 700 nm, and the infrared wavelength may be between about 800 nm and about 1000 nm. In embodiments where a sensor array is used in place of single sensor, each sensor may be configured to emit a single wavelength. For example, a first sensor may emit a red light while a second sensor may emit an infrared light.

As discussed above, the PPG system 210 is described in terms of a pulse oximetry system. However, the PPG system 210 may be various other types of systems. For example, the PPG system 210 may be configured to emit more or less than two wavelengths of light into the tissue 240 of the patient. Further, the PPG system 210 may be configured to emit wavelengths of light other than red and infrared into the tissue 240. As used herein, the term "light" may refer to energy produced by radiative sources and may include one or more of ultrasound, radio, microwave, millimeter wave, infrared, visible, ultraviolet, gamma ray or X-ray electromagnetic radiation. The light may also include any wavelength within the radio, microwave, infrared, visible, ultraviolet, or X-ray spectra, and that any suitable wavelength of electromagnetic radiation may be used with the system 210. The detector 218 may be configured to be specifically sensitive to the chosen targeted energy spectrum of the emitter 216.

The detector 218 may be configured to detect the intensity of light at the red and infrared wavelengths. Alternatively, each sensor in the array may be configured to detect an intensity of a single wavelength. In operation, light may enter the detector 218 after passing through the tissue 240. The detector 218 may convert the intensity of the received light into an electrical signal. The light intensity may be directly related to the absorbance and/or reflectance of light in the tissue 240. For example, when more light at a certain wavelength is absorbed or reflected, less light of that wavelength is received from the tissue by the detector 218. After converting the received light to an electrical signal, the detector 218 may send the signal to the monitor 214, which calculates physiological parameters based on the absorption of the red and infrared wavelengths in the tissue 240.

In an embodiment, an encoder 242 may store information about the sensor 212, such as sensor type (for example, whether the sensor is intended for placement on a forehead or digit) and the wavelengths of light emitted by the emitter 216. The stored information may be used by the monitor 214 to select appropriate algorithms, lookup tables and/or calibration coefficients stored in the monitor 214 for calculating physiological parameters of a patient. The encoder 242 may store or otherwise contain information specific to a patient, such as, for example, the patient's age, weight, and diagnosis. The information may allow the monitor 214 to determine, for example, patient-specific threshold ranges related to the patient's physiological parameter measurements, and to enable or disable additional physiological parameter algorithms. The encoder 242 may, for instance, be a coded resistor that stores values corresponding to the type of sensor 212 or the types of each sensor in the sensor array, the wavelengths of light emitted by emitter 216 on each sensor of the sensor array, and/or the patient's characteristics. Optionally, the encoder 242 may include a memory in which one or more of the following may be stored for communication to the monitor 214: the type of the sensor 212, the wavelengths of light emitted by emitter 216, the particular wavelength each sensor in the sensor array is monitoring, a signal threshold for each sensor in the sensor array, any other suitable information, or any combination thereof.

Signals from the detector 218 and the encoder 242 may be transmitted to the monitor 214. The monitor 214 may include a general-purpose control unit, such as a microprocessor 248 connected to an internal bus 250. The microprocessor 248 may be configured to execute software, which may include an operating system and one or more applications, as part of performing the functions described herein. A read-only memory (ROM) 252, a random access memory (RAM) 254, user inputs 256, the display 220, and the speaker 222 may also be operatively connected to the bus 250. The control unit and/or the microprocessor 248 may include a cardiac stability analysis module 249 that is configured to determine a trending nature, index or value of the PPG signals or waveform to determine cardiac stability of the patient. In an embodiment, the cardiac stability analysis module 249 analyzes the PPG signal to determine a variance in amplitude of the PPG signal of one or more pulses over a time period as a basis for determining the cardiac stability of the patient. The cardiac stability analysis module 249 is configured to determine a cardiac stability ratio of the amplitude variance with respect to a pulse period variance based on calculations, measurements or other information, data or signals received from the PPG sensor 212 or other components of the system 200.

The RAM 254 and the ROM 252 are illustrated by way of example, and not limitation. Any suitable computer-readable media may be used in the system for data storage. Computer-readable media are configured to store information that may be interpreted by the microprocessor 248. The information may be data or may take the form of computer-executable instructions, such as software applications, that cause the microprocessor to perform certain functions and/or computer-implemented methods. The computer-readable media may include computer storage media and communication media. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which may be used to store desired information and that may be accessed by components of the system.

The monitor 214 may also include a time processing unit (TPU) 258 configured to provide timing control signals to a light drive circuitry 260, which may control when the emitter 216 is illuminated and multiplexed timing for the red LED 244 and the infrared LED 246. The TPU 258 may also control the gating-in of signals from the detector 218 through an amplifier 262 and a switching circuit 264. The signals are sampled at the proper time, depending upon which light source is illuminated. The received signal from the detector 218 may be passed through an amplifier 266, a low pass filter 268, and an analog-to-digital converter 270. The digital data may then be stored in a queued serial module (QSM) 272 (or buffer) for later downloading to RAM 254 as QSM 272 fills up. In an embodiment, there may be multiple separate parallel paths having amplifier 266, filter 268, and A/D converter 270 for multiple light wavelengths or spectra received.

The microprocessor 248 may be configured to determine the patient's physiological parameters, such as cardiac stability, amplitude, variance in amplitude, pulse period, variance in pulse period, SV, CO, SpO2, pulse rate, and the like, using various algorithms and/or look-up tables based on the value(s) of the received signals and/or data corresponding to the light received by the detector 218. The signals corresponding to information about a patient, and regarding the intensity of light emanating from the tissue 240 over time, may be transmitted from the encoder 242 to a decoder 274. The transmitted signals may include, for example, encoded information relating to patient characteristics. The decoder 274 may translate the signals to enable the microprocessor 248 to determine the thresholds based on algorithms or look-up tables stored in the ROM 252. The user inputs 256 may be used to enter information about the patient, such as age, weight, height, diagnosis, medications, treatments, and so forth. The display 220 may show a list of values that may generally apply to the patient, such as, for example, age ranges or medication families, which the user may select using the user inputs 256.

As noted, the PPG system 210 may be a pulse oximetry system. A pulse oximeter is a medical device that may determine oxygen saturation of blood. The pulse oximeter may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of a patient. Pulse oximeters typically measure and display various blood flow characteristics including, but not limited to, the oxygen saturation of hemoglobin in arterial blood.

A pulse oximeter may include a light sensor, similar to the sensor 212, which is placed at a site on a patient, typically a fingertip, toe, forehead or earlobe, or in the case of a neonate, across a foot. The pulse oximeter may pass light using a light source through blood perfused tissue and photoelectrically sense the absorption of light in the tissue. For example, the pulse oximeter may measure the intensity of light that is received at the light sensor as a function of time. A signal representing light intensity versus time or a mathematical manipulation of this signal (for example, a scaled version thereof, a log taken thereof, a scaled version of a log taken thereof, and/or the like) may be referred to as the photoplethysmogram (PPG) signal. In addition, the term "PPG signal," as used herein, may also refer to an absorption signal (for example, representing the amount of light absorbed by the tissue) or any suitable mathematical manipulation thereof. The light intensity or the amount of light absorbed may then be used to calculate the cardiac stability, amplitude, variance in amplitude, pulse period, variance in pulse period as well as other physiological parameter when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with lower oxygen saturation. By comparing the intensities of two wavelengths at different points in the pulse cycle, it is possible to estimate the blood oxygen saturation of hemoglobin in arterial blood.

Cardiac stability may correlate with cardiac health and other physiological parameters important in patient care, such as hypovolemia, fluid responsiveness, and the like. Hypovolemia relates to a decrease in blood volume and may correspond to hemorrhaging of the patient. Fluid responsiveness relates to the volume of fluid, such as blood, in the arteries, veins, and vasculature of an individual. Fluid responsiveness also relates to hemorrhaging. In general, fluid responsiveness may include a measurement of the response of stroke volume, the volume of blood passing out of the heart with each heartbeat, to venous return, the volume of blood entering the heart with each heartbeat, caused by the clinical administration of fluid into the vasculature, such as through an intravenous injection. With each heartbeat, a certain amount of blood is pumped out of the heart. The more blood that fills the heart, the more blood the heart can pump out with each heartbeat. If blood volume is too low, the heart may not fully fill with blood. Therefore, the heart may not pump out as much blood with each heartbeat. Consequently, low blood volume may lead to low blood pressure, and organs and tissues may not receive enough blood to optimally and/or properly function. Monitoring cardiac stability may allow a physician to determine whether a patient is hemorrhaging or otherwise requires additional fluid more quickly than noticing a decrease in blood pressure. In short, cardiac stability represents a prediction of whether or not a decrease in blood pressure is occurring.

Cardiac stability may be monitored in, for example, critically-ill patients or trauma patients because fluid administration plays an important role in optimizing cardiac output and stability for proper oxygen delivery to organs and tissues. Trauma patients are generally at greater risk of hemorrhaging, and the hemorrhage may occur internally or at sites that are unnoticeable to the physician. Therefore, obtaining reliable information and parameters that aid clinicians in early detection of hemorrhaging may help improve patient outcomes.

Figure 4:
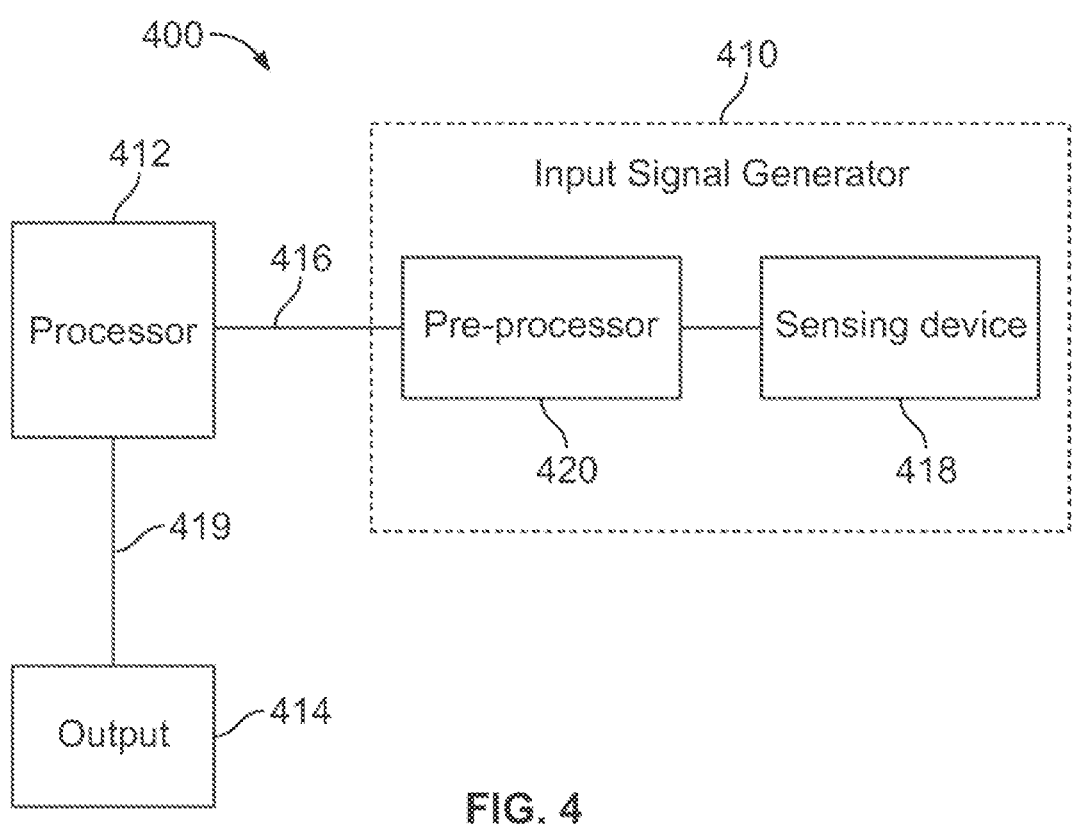
FIG. 4 is an illustrative processing system in accordance with an embodiment.

FIG. 4 is an illustrative processing system 400 in accordance with an embodiment. In an embodiment, an input signal generator 410 generates an input signal 416. The input signal generator 410 includes a pre-processor 420 coupled to a sensing device 418. It will be understood that the input signal generator 410 may include any suitable signal source, signal generating data, signal generating equipment, or any combination thereof to produce the signal 416. The signal 416 may be a single signal, or may be multiple signals transmitted over a single pathway or multiple pathways.

The pre-processor 420 may apply one or more signal processing techniques to the signal generated by the sensing device 418. For example, the pre-processor 420 may apply a pre-determined transformation to the signal provided by the sensing device 418 to produce an input signal 416 that can be appropriately interpreted by the processor 412. The pre-processor 420 may also perform any of the following operations to the signal provided by the sensing device 418: reshaping the signal for transmission; multiplexing the signal; modulating the signal onto carrier signals; compressing the signal; encoding the signal; and filtering the signal.

In the embodiment of FIG. 4, the signal 416 is coupled to the processor 412. The processor 412 may be any suitable software, firmware, and/or hardware, and/or combinations thereof for processing the signal 416. For example, the processor 412 may include one or more hardware processors (e.g., integrated circuits), one or more software modules, computer-readable media such as memory, firmware, or any combination thereof. The processor 412 may, for example, be a computer or may be one or more chips (i.e., integrated circuits). The processor 412 may, for example, be configured of analog electronic components. The processor 412 may perform some or all of the calculations associated with the monitoring methods of the present disclosure. For example, the processor 412 may analyze the physiological signals, waveforms, and the like and compute pulse trending characteristics thereof to determine a cardiac stability ratio and associated cardiac stability of the patient, as discussed further below. The processor 412 may also perform any suitable signal processing to filter the signal 416, such as any suitable band-pass filtering, adaptive filtering, closed-loop filtering, and/or any other suitable filtering, and/or any combination thereof. The processor 412 may also receive input signals from additional sources (not shown). For example, the processor 412 may receive an input signal containing information about the patient or treatments provided to the patient. These additional input signals may be used by the processor 412 in any of the calculations or operations it performs in accordance with the processing system 400.

The processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. In an embodiment, the processor 412 may store physiological measurements or previously received data from the signal 416 in a memory device for later retrieval. The processor 412 may be coupled to a calibration device (not shown) that may generate or receive as input reference measurements for use in calibrating calculations.

The processor 412 is coupled to an output 414 through a patient status indicator signal 419, and may be coupled through additional signal pathways not shown. The output 414 may be any suitable output device such as, for example, one or more medical devices (e.g., a medical monitor that displays various physiological parameters, a medical alarm, or any other suitable medical device that either displays physiological parameters or uses the output of the processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof. In an embodiment, the patient status indicator signal 419 includes at least one of an identification of a medical condition of the patient; an alert; a current cardiac stability of the patient; a current stroke volume measurement; a current cardiac output measurement; a current HR measurement; a current BP measurement; another current physiological measurement; an estimated patient status; and an estimated patient outcome. In some embodiments, the patient status indicator signal 419 will be stored in a memory device or recorded in another physical form for future, further analysis.

It will be understood that the system 400 may be incorporated into the system 100 (shown in FIG. 1) and/or the system 210 (shown in FIGS. 2 and 3) in which, for example, the input signal generator 410 may be implemented as parts of the sensor 212 and/or the monitor 214 and the processor 412 may be implemented as part of the monitor 214. In some embodiments, portions of the system 400 may be configured to be portable. For example, all or a part of the system 400 may be embedded in a small, compact object carried with or attached to the patient (e.g., a watch, other piece of jewelry, or cellular telephone). In such embodiments, a wireless transceiver (not shown) may also be included in the system 400 to enable wireless communication with other components of system 210. As such, the system 210 may be part of a fully portable and continuous monitoring solution.

Figure 5:
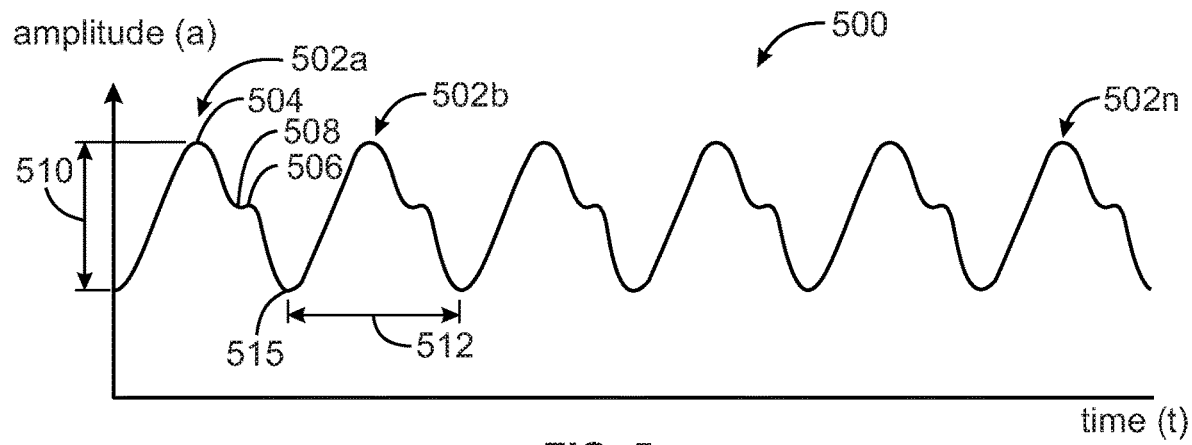
FIG. 5 illustrates a pulse waveform of a PPG signal, according to an embodiment.

FIG. 5 illustrates a PPG signal 500 over time, according to an embodiment. The PPG signal 500 is an example of a physiological signal. However, embodiments may be used in relation to various other physiological signals, such as electrocardiogram signals, phonocardiogram signals, ultrasound signals, and the like. The PPG signal 500 may be determined, formed, and displayed as a waveform by the monitor 214 (shown in FIG. 2) that receives signal data from the PPG sensor 212 (shown in FIG. 2). For example, the monitor 214 may receive signals from the PPG sensor 212 positioned on a finger of a patient. The monitor 214 processes the received signals, and displays the resulting PPG signal 500 on the display 228 (shown in FIG. 2).

The PPG signal 500 may include a plurality of pulses 502a-502n over a predetermined time period. The time period may be a fixed time period, or the time period may be variable. Moreover, the time period may be a rolling time period, such as a 5 second rolling timeframe.

Each pulse 502a-502n may represent a single heartbeat and may include a pulse-transmitted or primary peak 504 separated from a pulse-reflected or trailing peak 506 by a dichrotic notch 508. The primary peak 504 represents a pressure wave generated from the heart to the point of detection, such as in a finger where the PPG sensor 212 is positioned. The trailing peak 506 represents a pressure wave that is reflected from the location proximate where the PPG sensor 212 is positioned back toward the heart. Characteristics of the primary peak 504 and/or the trailing peak 506 may be analyzed by the cardiac stability analysis module 249 (shown in FIG. 3) to calculate the cardiac stability ratio or other physiological parameters of the patient.

As shown in FIG. 5, each pulse 502a-502n has a particular amplitude. For example, the pulse 502a has an amplitude 510 (e.g., an overall amplitude or absolute amplitude). Although shown having uniform amplitudes 510 to facilitate discussion, the amplitudes 510 of each pulse 502a-502n may differ with respect to one another. In general, the amplitude 510 of each pulse 502a-502n of the PPG signal 500 over time t may modulate. The cardiac stability analysis module 249 (shown in FIG. 3) of the monitor 214 may track and store the magnitude of the amplitude modulation of the PPG signal 500 over time t. Optionally, the cardiac stability analysis module 249 of the monitor 214 may track and store the magnitude of the amplitude 510 of any number of the pulses 502a-502n for use in determining a cardiac stability ratio or other physiological parameter of the patient. For example, the cardiac stability analysis module 249 of the monitor 214 may use a single pulse 502a, analyze the single pulse to determine a trending nature of the waveform thereof relative to previous pulses, and calculate the cardiac stability ratio or other physiological parameter of the patient based on the single pulse 502a. Alternatively, the cardiac stability analysis module 249 may use multiple pulses 502a-502n, analyze the trending nature of the waveforms thereof relative to previous or baseline waveforms, and calculate the cardiac stability ratio or other physiological parameter of the patient based upon a comparison of the amplitudes, pulse periods or other aspects of the waveforms of the pulses 502a-502n to calculate the cardiac stability ratio or other physiological parameter of the patient. Optionally, the cardiac stability analysis module 249 of the monitor 214 may determine an average modulation of the pulses 502a-502n over a time period t and use the average modulation to calculate the cardiac stability ratio or other physiological parameter of the patient.

The frequency of the pulses 502a-502n may vary. For example, the frequency of the pulses over a first period of time may vary from a frequency over a later period of time. The monitor 214 (shown in FIG. 2) may monitor and determine the frequencies. The frequency variation may be based upon respiration, blood pressure, heart rate, or other factors. The cardiac stability analysis module 249 of the monitor 214 may detect a magnitude of frequency modulation over a time period t. The cardiac stability analysis module 249 of the monitor 214 may use the frequency of the pulses, or any other temporal element of the pulses, to analyze the trending nature of the waveforms thereof, and calculate the cardiac stability ratio or other physiological parameter of the patient.

Various waveform characteristics may be measured and/or calculated from the pulse waveform of the PPG signal 500. The waveform characteristics may be used by the cardiac stability analysis module 249 (shown in FIG. 3) to calculate the cardiac stability ratio or other physiological parameter of the patient. For example, as described in further detail below, the cardiac stability analysis module 249 may utilize a pulse period, a transit time, an amplitude, a peak, a temporal element, a change in any of the waveform characteristics, and the like to calculate the cardiac stability ratio or other physiological parameter of the patient.

A pulse transit time (PTT) is a measure of a temporal element of the pulse. For example, the PTT may be a transit time of a given pulse from the heart to the location proximate where the PPG sensor 212 is positioned. The PTT may be calculated by using an ECG system to detect the pulse at the heart and a PPG system to detect the pulse at the finger, and the time difference between the detection at the heart and the detection at the finger corresponds to the PPT. The PTT may be calculated by using a dual-pleth system where two PPG sensors are attached at two different locations of the patient and measuring a differential time between detection of the pulse at the first PPG sensor and detection of the pulse at the second PPG sensor (e.g. at a finger and at an ear). The time difference between the pulse detections correspond to the PPT. Other methods of detecting and/or calculating the PPT may be used in other embodiments. The PPT may be affected by other physiological conditions of the patient, such as blood pressure, heart rate, respiration, and the like. The PTT is variable depending on the physiological status of the patient.

A pulse period 512, defined by the heart rate (HR) of the patient, may be calculated by measuring the time difference between the pulses. For example, the pulse period 512 may be a measurement of the time difference from the initiation of one pulse 502a to the initiation of the second pulse 502b. Alternatively, the pulse period 512 may be a measurement of the time difference from the peak 504 of the pulse 502a to the peak 504 of the second pulse 502b. The pulse period 512 may be affected by other physiological conditions of the patient, such as blood pressure, heart rate, respiration, and the like. The pulse period 512 is variable depending on the physiological status of the patient.

The PPG signal 500 shown in FIG. 5 corresponds to a steady heart. The cardiac stability and function are generally normal and healthy. The steady heart is characterized as being regular (e.g. the pulse periods 512 are similar over time) and consistent (e.g. the amplitudes 510 have high variance from the mean amplitude). The peaks and troughs characteristic of the steady heart are generally far apart (e.g. have high variance from the mean amplitude 511). An unsteady heart is generally the opposite of a steady heart. The unsteady heart is characterized as being irregular (e.g. the pulse periods 512 tend to change form beat to beat) and inconsistent (e.g. the amplitudes 510 tend to have a smaller variance from the mean amplitude over time, such as when the peaks and troughs are closer to the mean amplitude).

Figure 6:
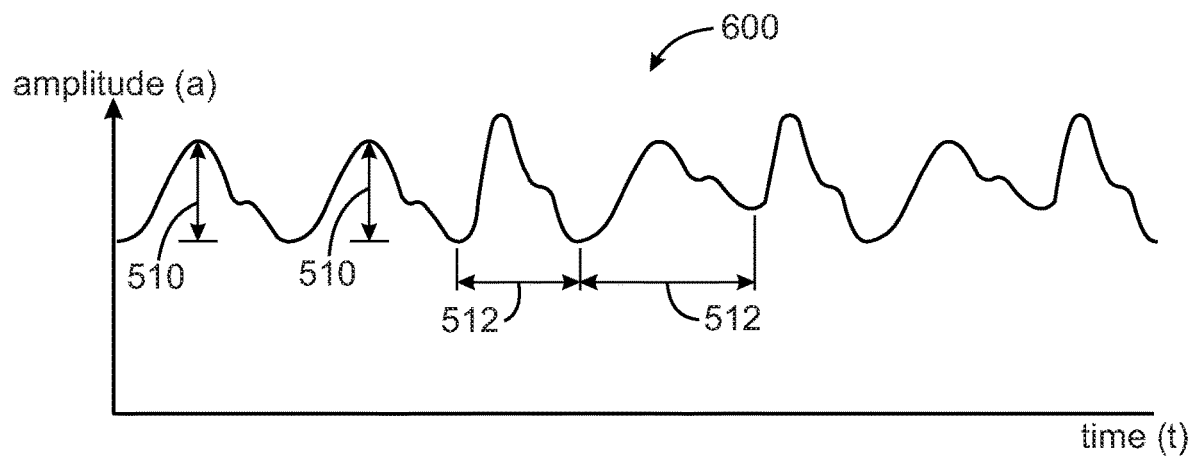
FIG. 6 illustrates a pulse waveform of a PPG signal, according to an embodiment.

FIG. 6 illustrates a PPG signal 600 over time, according to an embodiment. The PPG signal 600 corresponds to an unsteady heart. Features of the PPG signal 600 that correspond to like features of the PPG signal 500 are identified with like reference numerals (e.g. amplitude 510 and pulse period 512). A comparison of the PPG signal 500 showing an embodiment of a steady heart can be seen with additional reference to FIG. 5. The steady heart shows strong (e.g., relatively high) statistical variance around the average amplitude between the peak absorptions (e.g., peaks 504) and the minimum absorptions (e.g., troughs 515) associated with each pulse 502a-502n.

In an embodiment, characteristics of the PPG signals 500, 600 may be useful in determining a cardiac stability ratio to determine cardiac stability of the patient. For example, the cardiac stability analysis module 249 may use the amplitudes 510 of the primary peaks 504 to calculate cardiac stability or other physiological parameters of the patient. The cardiac stability analysis module 249 may use the pulse periods 512 of the pulses to calculate cardiac stability or other physiological parameters of the patient. The cardiac stability analysis module 249 may determine a cardiac stability ratio based on variance in amplitude 510 and variance in pulse period 512 over time. For example, the cardiac stability analysis module 249 may determine a cardiac stability ratio (CSR) based on the following:

$$CSR=(V(A))/V(PP) \quad \text{Equation (1)}$$

where V(A) is the variance of the amplitude of the pulse(s) and V(PP) is the variance of the pulse period of the pulse. The cardiac stability analysis module 249 may determine the CSR for each individual pulse and compare the pulse to previous pulses to determine the amplitude and pulse period variances thereof. Alternatively, the cardiac stability analysis module 249 may determine the CSR for multiple pulses over a predetermined time. Optionally, the cardiac stability analysis module 249 may continuously determine the CSR over a predetermined time period.

The variance of the amplitude V(A) may be the average of the squares of difference between the amplitudes of the pulses (e.g., amplitude 510) and the mean amplitude of the pulses. For example, the variance of the amplitude V(A) may be determined by the cardiac stability analysis module 249 based on the following:

$$\frac{\Sigma(\text{each pulse amplitude} - \text{average pulse amplitude})^2}{\text{number of pulses in time } t} \quad \text{Equation (2)}$$

The variance of the pulse period V(PP) may be the average of the squares of difference between the pulse period of each pulses and the mean pulse period of the pulses. For example, the variance of the pulse period V(PP) may be determined by the cardiac stability analysis module 249 based on the following:

$$\frac{\Sigma(\text{each pulse period} - \text{average pulse period})^2}{\text{number of pulses in time } t} \quad \text{Equation (3)}$$

Alternatively, the cardiac stability analysis module 249 may determine the CSR based on a range (e.g. maximum amplitude−minimum amplitude) over a period of time and/or a range (e.g. maximum pulse period−minimum pulse period) over a period of time rather than the variances thereof. Using the ranges may provide a less sensitive tool, however the CSR may be determined more quickly, more frequently and/or with less computing power.

The CSR determined by the cardiac stability analysis module 249 provides an index that decreases quickly as cardiac capability decreases. For example, as the heart becomes unsteady, the variance of the amplitude V(A) will decrease. Because the CSR varies proportionally with respect to the variance of the amplitude V(A), as the variance of the amplitude V(A) decreases, the numerator of Equation 1 will decrease. Similarly, as the heart becomes unsteady, the variance of the pulse period V(PP) will increase. Because the CSR varies inversely with respect to the variance of the pulse period V(PP), as the variance of the pulse period V(PP) increases, the denominator of Equation 1 will increase, causing the CSR to decrease. Having both the numerator and the denominator cause the CSR to decrease as the heart becomes unsteady, the CSR is sensitive to changes in the cardiac stability.

Conversely, CSR determined by the cardiac stability analysis module 249 provides an index that increases as heart becomes steady. For example, as the heart becomes steady, the variance of the amplitude V(A) will increase causing the numerator of Equation 1 to increase. Similarly, as the heart becomes steady, the variance of the pulse period V(PP) will decrease causing the denominator of Equation 1 to decrease.

The cardiac stability analysis module 249 may calculate cardiac stability (CS) of the patient based on the CSR. For example, the CSR may be determined based on the following:

$$CS=(CSR)K \quad \text{Equation (4)}$$

where K is a scaling factor based on empirically-determined constants that may be determined through clinical examinations of patients, a calibration constant, the nature of the subject and/or the nature of the signal detecting devices. The scaling factor K may be computed from relationships derived from observed historical data (e.g., relationships with patient demographic data such as body mass index (BMI), height, weight, and the like) and/or measured signal characteristics (e.g., heart rate, PTT, amplitude, pulse period, and the like).

In some embodiments, the PPG signal may be corrected or normalized to account for changes in vascular tone and/or motion artifacts through analysis of the PPG signal. Normalizing may be performed prior to calculating K.

The CS determined by the cardiac stability analysis module 249 is displayed on the monitor 214 of the system 200 for use by the physician in analyzing the health of the patient and/or treating the patient. The scaling factor K may be selected to correlate the cardiac stability CS with a healthy or nominal number, such as 100. Having the CS decrease from the nominal number as the heart becomes unsteady provides a logical indicator for a physician to monitor. The displayed CS may be treated as a percentage of the nominal number where a CS of 70, for example, is an indication to the physician that the patient is having problems with cardiac functionality. Optionally, the cardiac stability analysis module 249 may store a threshold CS level, below which the system 200 may provide an alarm condition, such as an audible alarm, a visual alarm, or another type of alarm.

Figure 7:
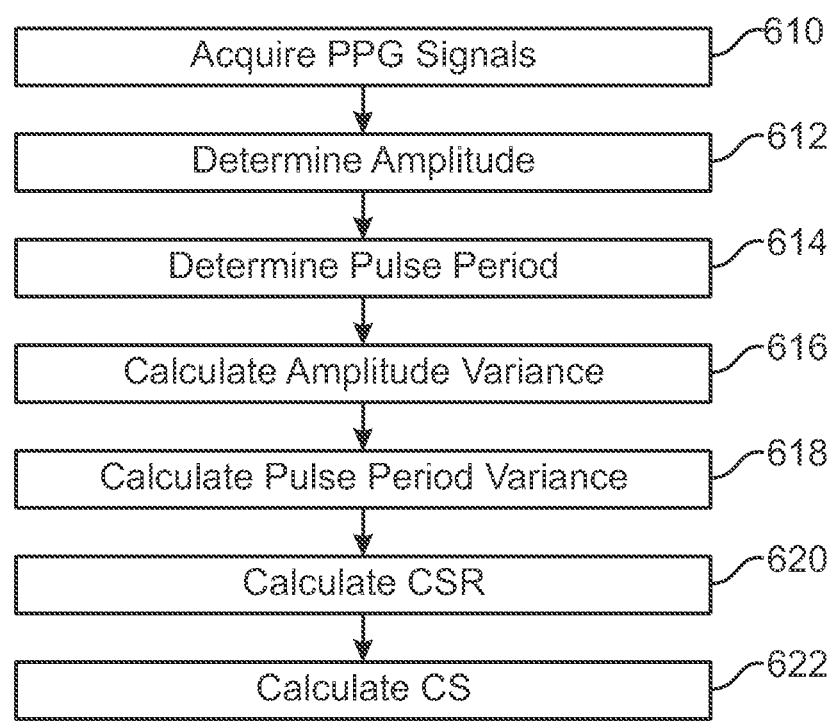
FIG. 7 illustrates a flow chart of a method of determining cardiac stability of a patient, according to an embodiment.

FIG. 7 illustrates a flow chart of a method of determining cardiac stability of a patient, according to an embodiment. The method may be performed by various systems, such as the system 100 (shown in FIG. 1), the system 210 (shown in FIGS. 2 and 3), or other capable systems. The method may include acquiring a physiological signal, such as a PPG signal, at step 610.

In step 612, the cardiac stability analysis module 249 analyzes the PPG signal to determine an amplitude (e.g., amplitude 510) of one or more pulses of the PPG signal. Then, at step 614, the PPG signal is analyzed to determine a pulse period of each pulse of the PPG signal.

At step 616, the system calculates the variance of the amplitudes of the pulses for a certain time period. For example, the system may calculate the average of the squared differences of the amplitudes (e.g., amplitude 510) from the mean amplitude. The system may calculate the variance of the amplitudes according to equation 2.

At step 618, the system calculates the variance of the pulse periods of the pulses for a certain time period. For example, the system may calculate the average of the squared differences of the pulse periods from the mean pulse period. The system may calculate the variance of the pulse periods according to equation 3.

At step 620, the system calculates the CSR based on the variance of the amplitudes of the pulses and the variance of the pulse periods of the pulses determined in steps 616 and 618, respectively. The CSR may be calculated according to equation 1. Further, the system, at step 622, may calculate the cardiac stability (CS) based on the CSR. For example, a scaling factor may be used to adjust the CSR to calculate a meaningful cardiac stability. The CS may be calculated according to equation 4.

Figure 8:
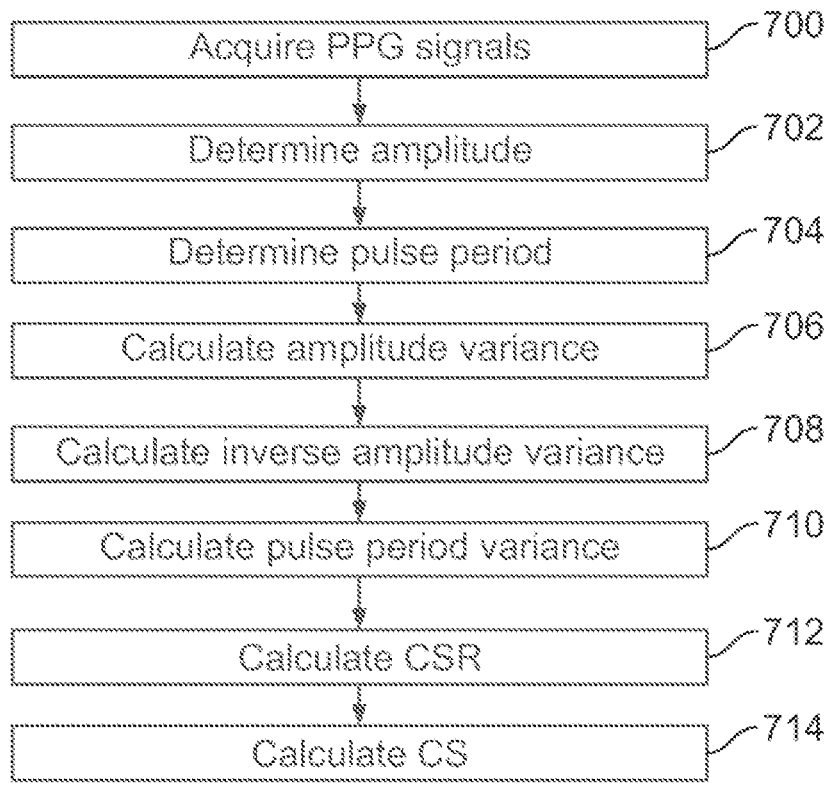
FIG. 8 illustrates a flow chart of another method of determining cardiac stability of a patient, according to an embodiment.

FIG. 8 illustrates a flow chart of another method of determining cardiac stability of a patient, according to an embodiment. The method may be performed by various systems, such as the system 100 (shown in FIG. 1), the system 210 (shown in FIGS. 2 and 3), or other capable systems. The method may include acquiring at 700 PPG signals. The PPG signals may be acquired by securing a PPG sensor to an anatomical portion of the patient and sensing a physiological characteristic of the patient with the PPG sensor. While the embodiment of the method described herein references acquiring PPG signals, such as using the PPG sensor 212 (shown in FIG. 2), the method may include acquiring other types of physiological signals, such as ECG signals, PCG signals, and/or ultrasound signals that characterize or describe cardiac activity. The physiological signals may be obtained from the individual for at least a designated period of time.

In an embodiment, the PPG signal is analyzed by the cardiac stability analysis module 249 (shown in FIG. 3). The cardiac stability analysis module 249 analyzes the PPG signal to determine waveform characteristics of the PPG signal, such as an amplitude of the PPG signal and a pulse period of the PPG signal for one or more pulses. For example, at 702, the PPG signal is analyzed to determine an amplitude of each primary peak of the PPG signal. Then, at 704, the PPG signal is analyzed to determine a pulse period of each pulse of the PPG signal.

At 706, the system calculates the variance of the amplitudes of the pulses for a certain time period, such as over 60 seconds. For example, the system may calculate the average of the squared differences of the amplitudes from the mean amplitude (e.g., an average of the amplitudes of the pulses 502a-502n). The system may calculate the variance of the amplitudes according to equation 2. At 708, the system calculates the inverse variance of the amplitudes calculated at 706. The inverse variance is used to determine the cardiac stability ratio (CSR).

At 710, the system calculates the variance of the pulse periods of the pulses for a certain time period, such as over 60 seconds. For example, the system may calculate the average of the squared differences of the pulse periods from the mean pulse period. The system may calculate the variance of the pulse periods according to equation 3. The variance of the pulse periods is used to determine the cardiac stability ratio (CSR).

At 712, the system calculates the CSR based on the amplitudes and the pulse periods of the pulses. For example, the system may calculate the CSR using the inverse variance of the amplitudes of the pulses determined at step 708 and the variance of the pulse periods of the pulses determined at step 710 over a certain time period to calculate the CSR. The CSR may be calculated according to equation 1. The CSR may be calculated with a pleth-only system. For example, the system may be operated without the need for an invasive monitoring system, an ECG or any other monitoring system. The system may calculate the CSR with the use of a single PPG sensor. Further, the system, at 714, may calculate the cardiac stability (CS) based on the CSR. For example, a scaling factor may be used to adjust the CSR to calculate a meaningful cardiac stability. The CS may be calculated according to equation 4.

Figure 9:
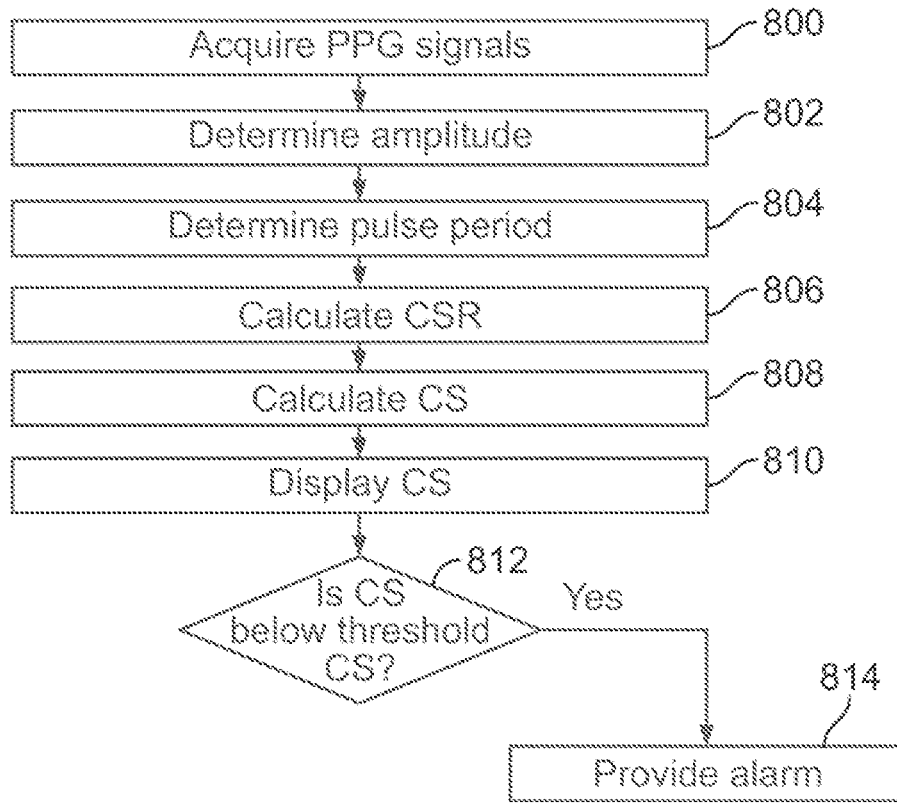
FIG. 9 illustrates a flow chart of a method of operating a PPG system, according to an embodiment.

FIG. 9 illustrates a flow chart of a method of operating a PPG system, according to an embodiment. The method may be performed by various systems, such as the system 100 (shown in FIG. 1), the system 210 (shown in FIGS. 2 and 3), or other capable systems. The method may include acquiring at 800 PPG signals. In an embodiment, the PPG signal is analyzed by the cardiac stability analysis module 249 (shown in FIG. 3). The cardiac stability analysis module 249 analyzes the PPG signal to determine waveform characteristics of the PPG signal.

At 802, the PPG signal is analyzed to determine an amplitude (e.g., the amplitude 510 of the primary peak of each pulse). At 804, the PPG signal is analyzed to determine a pulse period of each pulse. Then, at 806, a cardiac stability ratio (CSR) is calculated based on the amplitudes and pulse periods of the pulses over a period of time. In some embodiments, as discussed above with respect to FIG. 8, the CSR is calculated as a function of the inverse variance of the amplitudes. The CSR is calculated as a function of the variance of the pulse periods. The CSR may be calculated according to equation 1.

At 808, the system calculates a cardiac stability (CS) of the patient. The CS may be based on the CSR. For example, a scaling factor may be used to adjust the CSR to calculate a meaningful cardiac stability. The CS may be calculated according to equation 4.

At 810, the system displays the CS on a monitor, such as the monitor 214 (shown in FIG. 2). The CS may be displayed as a number, a grade, a graphical representation, and the like.

At 812, the system determines if the CS is below a threshold. The threshold may be based on physiological conditions of the patient, such as age, weight, height, diagnosis, medications, treatments, and so forth. If the CS falls below the threshold, the system at 814 provides an alarm condition. The alarm may be a visual alarm, an audible alarm, or another type of alarm. The alarm may be triggered on the monitor 214 and/or may be transmitted to another location, such as a central monitoring station to alert medical professionals.

Various embodiments described herein provide a tangible and non-transitory (for example, not an electric signal) machine-readable medium or media having instructions recorded thereon for a processor or computer to operate a system to perform one or more embodiments of methods described herein. The medium or media may be any type of CD-ROM, DVD, floppy disk, hard disk, optical disk, flash RAM drive, or other type of computer-readable medium or a combination thereof.

The various embodiments and/or components, for example, the control units, modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer," "computing system," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "computing system".

The computer, computing system, or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

As discussed above, embodiments may provide a system and method of determining cardiac stability of a patient through analysis of physiological signals, such as PPG signals, by analyzing waveform characteristics of the PPG signal and calculating an amplitude variance and a pulse period variance of the PPG signal over time.

It is to be understood that the above description is intended to be illustrative, and not restrictive. For example, the above-described embodiments (and/or aspects thereof) may be used in combination with each other. In addition, many modifications may be made to adapt a particular situation or material to the teachings without departing from its scope. While the dimensions, types of materials, and the like described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means–plus-function format and are not intended to be interpreted based on 35 U.S.C. § 112, sixth paragraph, unless and until such claim limitations expressly use the phrase "means for" followed by a statement of function void of further structure.

The invention claimed is:

1. A monitor, comprising:
a memory configured to store information indicative of a threshold cardiac stability; and
a processor configured to execute instructions stored on the memory to:
receive a photoplethysmogram (PPG) signal from a PPG sensor, the PPG signal comprising a plurality of pulses each representing a heartbeat of a patient;
determine an amplitude variance of the plurality of pulses over a time period, wherein the amplitude variance comprises an average of squared differences of an amplitude of a peak of each pulse of the plurality of pulses from a mean amplitude of the plurality of pulses over the time period;
determine a pulse period variance of the PPG signal over the time period;
determine cardiac stability of the patient based on a ratio of the amplitude variance with respect to the pulse period variance; and output an indication of the cardiac stability of the patient when the cardiac stability crosses the threshold cardiac stability.

2. The monitor of claim 1, comprising light drive circuitry configured to drive a light emitter of the PPG sensor to emit light into a tissue of the patient to enable detection of the PPG signal by a detector of the PPG sensor.

3. The monitor of claim 1, wherein the PPG signal received from the PPG sensor is generated by a detector of the PPG sensor based on a portion of light from an emitter, of the PPG sensor, that passed through a tissue of the patient.

4. The monitor of claim 1, wherein determining the cardiac stability of the patient comprises calculating the cardiac stability as a product of the ratio and a scaling factor.

5. The monitor of claim 1, wherein determining the pulse period variance comprises determining an average of squared differences of each pulse period from a mean pulse period over the time period.

6. The monitor of claim 1, wherein to output the indication of cardiac stability, the processor is configured to activate an alarm when the cardiac stability crosses the threshold cardiac stability.

7. The monitor of claim 1, wherein the processor is configured to provide the indication of the cardiac stability of the patient via a display.

8. The monitor of claim 1, wherein the processor is configured to compare the determined cardiac stability to the threshold cardiac stability, and wherein to output the indication, the processor is configured to output the indication based on the comparison.

9. A method of determining cardiac stability of a patient, the method comprising:
receiving a photoplethysmogram (PPG) signal from a PPG sensor, the PPG signal comprising a plurality of pulses each representing a heartbeat of the patient at a processor of a monitor;
analyzing, using the processor, an amplitude component of the PPG signal to determine an amplitude of a peak of each pulse of the plurality of pulses, a mean amplitude of the plurality of pulses over a time period, and an amplitude variance of the plurality of pulses over the time period, wherein the amplitude variance comprises an average of squared differences of the amplitude of the peak of each pulse of the plurality of pulses from the mean amplitude over the time period;
analyzing a temporal component of the PPG signal to determine a pulse period variance of the PPG signal over the time period, using the processor;
calculating a cardiac stability index of the patient based on a ratio of the amplitude variance with respect to the pulse period variance, using the processor;
determining that the stability index crosses a threshold cardiac stability; and
outputting an indication of cardiac stability of the patient when the cardiac stability index crosses the threshold cardiac stability.

10. The method of claim 9, comprising providing light from an emitter of the PPG sensor that passes through a tissue of the patient to enable generation of the PPG signal.

11. The method of claim 10, comprising, using a detector of the PPG sensor, detecting the light from the emitter that passes through the tissue of the patient, generating the PPG signal based on a portion of the light from the emitter that passes through the tissue of the patient, and providing the PPG signal to the processor of the monitor.

12. The method of claim 9, comprising generating a light drive signal using a light drive circuitry of the monitor to cause an emitter of the PPG sensor to provide light to a tissue of the patient to enable generation of the PPG signal.

13. The method of claim 9, comprising calculating the cardiac stability index as a product of the ratio and a scaling factor.

14. The method of claim 9, comprising determining the pulse period variance as an average of squared differences of a pulse period of the at least one pulse of the plurality of pulses from a mean pulse period over the time period.

15. A system configured to determine cardiac stability of a patient, the system comprising at least one processor configured to execute instructions stored on a memory to:
receive a physiological signal indicative of cardiac function from a medical sensor, wherein the physiological signal comprises a plurality of pulses;
determine an amplitude variance of the physiological signal over a time period and a pulse period variance of the physiological signal over the time period, wherein the amplitude variance comprises a statistical variance of an amplitude of a peak of each pulse of the plurality of pulses from a mean amplitude of the plurality of pulses over the time period;
determine a cardiac stability index based on a cardiac stability ratio, wherein the cardiac stability ratio is a function of the amplitude variance and the pulse period variance; and
output an indication of the cardiac stability of the patient when the cardiac stability index crosses a threshold cardiac stability stored in the memory.

16. The system of claim 15, wherein the physiological signal comprises one or more of a photoplethysmogram (PPG) signal, an electrocardiogram (ECG) signal, a phonocardiogram (PCG) signal, or an ultrasound signal.

17. The system of claim 15, comprising the medical sensor, wherein the medical sensor is configured to obtain the physiological signal and to provide the physiological signal to the at least one processor, wherein the medical sensor is a photoplethysmography (PPG) sensor comprising an emitter configured to emit light into a tissue of the patient and a detector configured to generate the physiological signal based on a portion of the light from the emitter that passed through the tissue of the patient.

18. The system of claim 15, wherein the at least one processor is configured to calculate the cardiac stability index as a product of the cardiac stability ratio and a scaling factor.

19. The system of claim 15, wherein the at least one processor is configured to determine the pulse period variance as an average of squared differences of each pulse period from a mean pulse period over the time period.

20. The system of claim 15, wherein to output the indication, at least one processor is configured to initiate an alarm when the cardiac stability index crosses the threshold cardiac stability.

21. The system of claim 15, wherein the cardiac stability ratio comprises a ratio of the amplitude variance with respect to the pulse period variance.

22. The system of claim 15, wherein the at least one processor is configured to determine an inverse of the amplitude variance, and wherein the cardiac stability ratio comprises a ratio of the inverse of the amplitude variance with respect to the pulse period variance.

* * * * *